(12) United States Patent
Cheng et al.

(10) Patent No.: US 7,746,978 B2
(45) Date of Patent: *Jun. 29, 2010

(54) PATH PLANNING AND COLLISION AVOIDANCE FOR MOVEMENT OF INSTRUMENTS IN A RADIATION THERAPY ENVIRONMENT

(75) Inventors: Chieh C. Cheng, Redlands, CA (US); David A. Lesyna, Redlands, CA (US); Michael F. Moyers, Colton, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/868,918

(22) Filed: Oct. 8, 2007

(65) Prior Publication Data

US 2008/0187097 A1    Aug. 7, 2008

Related U.S. Application Data

(63) Continuation of application No. 10/917,220, filed on Aug. 12, 2004, now Pat. No. 7,280,633.

(60) Provisional application No. 60/494,699, filed on Aug. 12, 2003, provisional application No. 60/579,095, filed on Jun. 10, 2004.

(51) Int. Cl.
    *A61N 5/10* (2006.01)
(52) U.S. Cl. .......................................... 378/65; 378/197
(58) Field of Classification Search .................... 378/65, 378/68, 69, 205, 209, 117, 195, 196, 197
    See application file for complete search history.

(56) References Cited

U.S. PATENT DOCUMENTS 2,469,084 A    5/1949    Schenker 2,675,564 A    4/1954    Hughes (Continued)

FOREIGN PATENT DOCUMENTS

DE    2513896    10/1975

(Continued)

OTHER PUBLICATIONS

"Dedicated Medical Ion Accelerator Design Study" by Lawrence Berkeley Laboratory, et al., Dec. 1977, PCTA008295-PCTA008455.

(Continued)

*Primary Examiner*—Hoon Song
(74) *Attorney, Agent, or Firm*—Knobbe, Martens, Olson & Bear, LLP

(57) ABSTRACT

A patient positioning system for use with a radiation therapy system that monitors the location of fixed and movable components and pre-plans movement of the movable components so as to inhibit movement if a collision would be indicated. The positioning system can also coordinate movement of multiple movable components for reduced overall latency in registering a patient. The positioning system includes external measurement devices which measure the location and orientation of objects, including components of the radiation therapy system, in space and can also monitor for intrusion into the active area of the therapy system by personnel or foreign objects to improve operational safety of the radiation therapy system.

21 Claims, 17 Drawing Sheets

U.S. PATENT DOCUMENTS

| | | |
|---|---|---|
| 3,397,411 A | 8/1968 | Rossi |
| 3,449,570 A | 6/1969 | Kok |
| 3,545,739 A | 12/1970 | D'Avignon |
| 3,556,455 A | 1/1971 | Storm |
| 3,604,931 A | 9/1971 | Kastner et al. |
| 3,640,787 A | 2/1972 | Heller |
| 3,689,949 A | 9/1972 | Weinstein et al. |
| 3,745,998 A | 7/1973 | Rose |
| 3,762,404 A | 10/1973 | Sakita |
| 3,778,049 A | 12/1973 | Viamonte, Jr. |
| 3,783,251 A * | 1/1974 | Pavkovich .................. 600/1 |
| 3,848,132 A | 11/1974 | Foderaro |
| 3,851,644 A | 12/1974 | Slagle |
| 3,885,258 A | 5/1975 | Regan |
| 3,893,198 A | 7/1975 | Blair |
| 3,897,345 A | 7/1975 | Foster |
| 3,897,777 A | 8/1975 | Morrison |
| 3,901,588 A | 8/1975 | Longhenry |
| 3,905,054 A | 9/1975 | Windsor et al. |
| 3,947,686 A | 3/1976 | Cooper et al. |
| 3,986,697 A | 10/1976 | Amor, Jr. et al. |
| 4,034,224 A | 7/1977 | Heavens et al. |
| 4,064,401 A | 12/1977 | Marden |
| 4,190,772 A | 2/1980 | Dinwiddie et al. |
| 4,230,129 A | 10/1980 | LeVeen |
| 4,252,594 A | 2/1981 | Cooper |
| 4,256,112 A | 3/1981 | Kopf et al. |
| 4,262,204 A | 4/1981 | Mirabella |
| 4,269,512 A | 5/1981 | Nosler |
| 4,287,425 A | 9/1981 | Elliot, Jr. |
| 4,327,046 A | 4/1982 | Davis et al. |
| 4,347,213 A | 8/1982 | Rogers, Jr. |
| 4,365,341 A | 12/1982 | Lam |
| 4,392,239 A | 7/1983 | Wilkens |
| 4,400,820 A | 8/1983 | O'Dell et al. |
| 4,450,122 A | 5/1984 | Gallina |
| 4,484,571 A | 11/1984 | Velazquez |
| 4,504,050 A | 3/1985 | Osborne |
| 4,552,508 A | 11/1985 | Reid |
| 4,578,757 A | 3/1986 | Stark |
| 4,591,341 A | 5/1986 | Andrews |
| 4,616,814 A | 10/1986 | Harwood-Nash et al. |
| 4,666,304 A | 5/1987 | Davies |
| 4,671,284 A | 6/1987 | Wilson et al. |
| 4,682,818 A | 7/1987 | Morell |
| 4,688,780 A | 8/1987 | Hanz |
| 4,705,955 A | 11/1987 | Mileikowsky |
| 4,711,578 A | 12/1987 | Chaimowicz |
| 4,752,064 A | 6/1988 | Voss |
| 4,779,858 A | 10/1988 | Saussereau |
| 4,796,613 A | 1/1989 | Heumann et al. |
| 4,819,257 A | 4/1989 | Grasser et al. |
| 4,841,965 A | 6/1989 | Jacobs |
| 4,905,267 A | 2/1990 | Miller et al. |
| 4,917,344 A | 4/1990 | Prechter et al. |
| 4,926,457 A | 5/1990 | Poehner et al. |
| 4,979,519 A | 12/1990 | Chavarria et al. |
| 5,014,290 A | 5/1991 | Moore et al. |
| 5,017,789 A | 5/1991 | Young et al. |
| 5,046,708 A | 9/1991 | Schaefer |
| 5,048,071 A | 9/1991 | Van Steenburg |
| 5,049,147 A | 9/1991 | Danon |
| 5,054,049 A | 10/1991 | Manabe |
| 5,081,665 A | 1/1992 | Kostich |
| 5,090,047 A | 2/1992 | Angotti et al. |
| 5,117,829 A | 6/1992 | Miller et al. |
| 5,156,166 A | 10/1992 | Sebring |
| 5,168,514 A | 12/1992 | Horton, Jr. et al. |
| 5,207,688 A | 5/1993 | Carol |
| 5,230,623 A | 7/1993 | Guthrie et al. |
| 5,240,218 A | 8/1993 | Dye |
| 5,242,455 A | 9/1993 | Skeens et al. |
| 5,269,305 A | 12/1993 | Corol |
| 5,276,927 A | 1/1994 | Day |
| 5,278,886 A | 1/1994 | Ohgushi et al. |
| 5,279,309 A | 1/1994 | Taylor et al. |
| 5,281,232 A | 1/1994 | Hamilton et al. |
| 5,287,576 A | 2/1994 | Fraser |
| 5,297,262 A | 3/1994 | Cox et al. |
| 5,361,765 A | 11/1994 | Herlihy et al. |
| 5,370,117 A | 12/1994 | McLaurin, Jr. |
| 5,370,118 A | 12/1994 | Vij et al. |
| 5,380,336 A | 1/1995 | Misko et al. |
| 5,388,580 A | 2/1995 | Sullivan et al. |
| 5,427,097 A | 6/1995 | Depp |
| 5,446,548 A | 8/1995 | Gerig et al. |
| 5,454,993 A | 10/1995 | Kostich |
| 5,464,411 A | 11/1995 | Schulte et al. |
| 5,485,833 A | 1/1996 | Dietz |
| 5,531,229 A | 7/1996 | Dean et al. |
| 5,538,494 A | 7/1996 | Matsuda |
| 5,549,616 A | 8/1996 | Schulte |
| 5,553,112 A | 9/1996 | Hardy et al. |
| 5,566,681 A | 10/1996 | Manwaring et al. |
| 5,570,409 A | 10/1996 | Yamaguchi et al. |
| 5,588,430 A | 12/1996 | Bova et al. |
| 5,595,191 A | 1/1997 | Kirk |
| 5,622,187 A | 4/1997 | Carol |
| 5,675,851 A | 10/1997 | Feathers |
| 5,676,673 A | 10/1997 | Ferre et al. |
| 5,727,554 A | 3/1998 | Kalend et al. |
| 5,745,545 A | 4/1998 | Hughes |
| 5,751,781 A | 5/1998 | Brown et al. |
| 5,771,512 A | 6/1998 | Kurakake et al. |
| 5,775,337 A | 7/1998 | Hauger et al. |
| 5,797,924 A | 8/1998 | Schulte et al. |
| 5,800,352 A | 9/1998 | Ferre et al. |
| 5,806,116 A | 9/1998 | Oliver et al. |
| 5,820,444 A | 10/1998 | McGaughey |
| 5,820,553 A | 10/1998 | Hughes |
| 5,823,192 A | 10/1998 | Kalend et al. |
| 5,832,550 A | 11/1998 | Hauger et al. |
| 5,848,449 A | 12/1998 | Hauger et al. |
| 5,851,182 A | 12/1998 | Sahadevan |
| 5,865,832 A | 2/1999 | Knopp et al. |
| 5,911,655 A | 6/1999 | Brenneisen |
| 5,947,981 A | 9/1999 | Cosman |
| 5,983,424 A | 11/1999 | Näslund |
| 6,003,174 A | 12/1999 | Kantrowitz et al. |
| 6,023,694 A | 2/2000 | Kouchi et al. |
| 6,026,392 A | 2/2000 | Kouchi et al. |
| 6,085,227 A | 7/2000 | Edlund et al. |
| 6,118,848 A | 9/2000 | Reiffel |
| 6,144,875 A | 11/2000 | Schweikard et al. |
| 6,144,993 A | 11/2000 | Fukunaga et al. |
| 6,148,272 A | 11/2000 | Bergstrom et al. |
| 6,161,237 A | 12/2000 | Tang et al. |
| 6,178,430 B1 | 1/2001 | Cohen et al. |
| 6,180,942 B1 | 1/2001 | Tracy et al. |
| 6,182,060 B1 | 1/2001 | Hedgcock et al. |
| 6,195,578 B1 | 2/2001 | Distler et al. |
| 6,200,025 B1 | 3/2001 | Rich |
| 6,244,745 B1 | 6/2001 | Mattern |
| 6,275,564 B1 | 8/2001 | Ein-Gal |
| 6,279,579 B1 | 8/2001 | Riaziat et al. |
| 6,282,739 B1 | 9/2001 | Livingston |
| 6,308,353 B1 | 10/2001 | Van Steenburg |
| 6,313,915 B1 | 11/2001 | Yanagisawa et al. |
| 6,325,758 B1 | 12/2001 | Carol et al. |
| 6,345,114 B1 | 2/2002 | Mackie et al. |
| 6,375,355 B1 | 4/2002 | Fortin |
| 6,376,846 B2 | 4/2002 | Livingston |
| 6,405,072 B1 | 6/2002 | Cosman |
| 6,446,286 B1 | 9/2002 | Karmalawy |

| | | |
|---|---|---|
| 6,452,999 B1 | 9/2002 | Maida |
| 6,462,553 B1 | 10/2002 | Badura |
| 6,473,490 B1 | 10/2002 | Siochi |
| 6,476,403 B1 | 11/2002 | Dolinskii et al. |
| 6,505,245 B1 | 1/2003 | North et al. |
| 6,509,573 B1 | 1/2003 | Badura et al. |
| 6,565,577 B2 | 5/2003 | Cosman |
| 6,598,275 B1 | 7/2003 | Kolody et al. |
| 6,614,038 B1 | 9/2003 | Brand et al. |
| 6,621,889 B1 | 9/2003 | Mostafavi |
| 6,650,930 B2 | 11/2003 | Ding |
| 6,662,036 B2 | 12/2003 | Cosman |
| 6,670,618 B1 | 12/2003 | Hartmann et al. |
| 6,677,597 B1 | 1/2004 | Haberer et al. |
| 6,690,965 B1 | 2/2004 | Riaziat et al. |
| 6,693,283 B2 | 2/2004 | Eickhoff et al. |
| 6,698,045 B1 | 3/2004 | Coppens et al. |
| 6,704,957 B2 | 3/2004 | Rhodes |
| 6,725,078 B2 | 4/2004 | Bucholz et al. |
| 6,754,299 B2 | 6/2004 | Patch |
| 6,769,806 B2 | 8/2004 | Moyers |
| 6,780,149 B1 | 8/2004 | Schulte |
| 6,795,523 B2 | 9/2004 | Steinberg |
| 6,799,068 B1 | 9/2004 | Hartmann et al. |
| 6,804,548 B2 | 10/2004 | Takahashi et al. |
| 6,813,788 B2 | 11/2004 | Dinkler et al. |
| 6,814,694 B1 | 11/2004 | Pedroni |
| 6,822,244 B2 | 11/2004 | Beloussov et al. |
| 6,839,404 B2 | 1/2005 | Clark et al. |
| 6,891,177 B1 | 5/2005 | Kraft et al. |
| 6,977,987 B2 | 12/2005 | Yamashita et al. |
| 7,011,447 B2 | 3/2006 | Moyers |
| 7,076,821 B2 | 7/2006 | DeMooy |
| 7,084,410 B2 | 8/2006 | Beloussov et al. |
| 7,120,223 B2 | 10/2006 | Näfstadius |
| 7,142,634 B2 | 11/2006 | Engler et al. |
| 7,154,108 B2 | 12/2006 | Tadokoro et al. |
| 7,154,991 B2 | 12/2006 | Earnst et al. |
| 7,173,265 B2 | 2/2007 | Miller et al. |
| 7,199,382 B2 | 4/2007 | Rigney et al. |
| 7,207,715 B2 | 4/2007 | Yue |
| 7,280,633 B2 | 10/2007 | Cheng et al. |
| 7,301,162 B2 | 11/2007 | Matsuda et al. |
| 7,331,713 B2 | 2/2008 | Moyers |
| 7,348,579 B2 | 3/2008 | Pedroni |
| 7,368,740 B2 | 5/2008 | Beloussov et al. |
| 7,372,053 B2 | 5/2008 | Yamashita et al. |
| 7,398,309 B2 | 7/2008 | Baumann et al. |
| 7,446,328 B2 | 11/2008 | Rigney et al. |
| 7,560,717 B2 | 7/2009 | Matsuda et al. |
| 2002/0032378 A1 | 3/2002 | Henderson et al. |
| 2002/0051513 A1 | 5/2002 | Pugachev et al. |
| 2002/0065461 A1 | 5/2002 | Cosman |
| 2002/0077545 A1 | 6/2002 | Takahashi et al. |
| 2002/0095730 A1 | 7/2002 | Al-Kassim et al. |
| 2002/0120986 A1 | 9/2002 | Erbel et al. |
| 2002/0188194 A1* | 12/2002 | Cosman ............... 600/426 |
| 2002/0193685 A1 | 12/2002 | Mate et al. |
| 2003/0007601 A1 | 1/2003 | Jaffray et al. |
| 2003/0031301 A1 | 2/2003 | Longton et al. |
| 2003/0164459 A1 | 9/2003 | Schardt et al. |
| 2004/0013414 A1 | 1/2004 | Karger et al. |
| 2004/0028188 A1 | 2/2004 | Amann et al. |
| 2004/0034438 A1 | 2/2004 | Uematsu |
| 2004/0034932 A1 | 2/2004 | Zacharopoulos et al. |
| 2004/0042583 A1 | 3/2004 | Wackerle et al. |
| 2004/0082856 A1 | 4/2004 | Marmarelis |
| 2004/0098445 A1 | 5/2004 | Baumann et al. |
| 2004/0098804 A1* | 5/2004 | Varadharajulu et al. ......... 5/611 |
| 2004/0123388 A1 | 7/2004 | Coppens et al. |
| 2004/0155206 A1 | 8/2004 | Marchand et al. |
| 2004/0158145 A1 | 8/2004 | Ghelmansarai et al. |
| 2004/0164254 A1 | 8/2004 | Beloussov et al. |
| 2004/0174958 A1 | 9/2004 | Moriyama et al. |
| 2004/0184583 A1 | 9/2004 | Nagamine et al. |
| 2005/0054910 A1 | 3/2005 | Tremblay et al. |
| 2005/0072940 A1 | 4/2005 | Beloussov et al. |
| 2005/0116175 A1 | 6/2005 | Haberer |
| 2005/0161618 A1 | 7/2005 | Pedroni |
| 2005/0226377 A1* | 10/2005 | Wong et al. ............ 378/65 |
| 2005/0281374 A1 | 12/2005 | Cheng et al. |
| 2006/0002511 A1 | 1/2006 | Miller et al. |
| 2006/0017022 A1 | 1/2006 | Rigney et al. |
| 2006/0183960 A1 | 8/2006 | Sioshansi et al. |
| 2007/0018120 A1 | 1/2007 | Beloussov et al. |
| 2007/0018121 A1 | 1/2007 | Leyman et al. |
| 2007/0025524 A1 | 2/2007 | Yue |
| 2007/0031337 A1 | 2/2007 | Schulte |
| 2007/0039621 A1 | 2/2007 | Moyers |
| 2007/0093100 A1 | 4/2007 | Sommer |
| 2007/0108922 A1 | 5/2007 | Amaldi |
| 2007/0158592 A1 | 7/2007 | Hiramoto et al. |
| 2007/0164230 A1 | 7/2007 | Rigney et al. |
| 2007/0262269 A1 | 11/2007 | Trbojevic |
| 2008/0005643 A1 | 1/2008 | Park et al. |
| 2008/0004207 A1 | 2/2008 | Miller et al. |
| 2008/0031414 A1 | 2/2008 | Coppens |
| 2008/0056434 A1 | 3/2008 | Grozinger et al. |
| 2008/0189859 A1 | 8/2008 | Sloan et al. |
| 2008/0191142 A1 | 8/2008 | Pedroni |
| 2008/0192892 A1 | 8/2008 | Dilmanian et al. |
| 2008/0237494 A1 | 10/2008 | Beloussov et al. |
| 2008/0292053 A1 | 11/2008 | Marash et al. |
| 2008/0317216 A1 | 12/2008 | Lifshitz et al. |
| 2009/0067577 A1 | 3/2009 | Rigney et al. |
| 2009/0154645 A1 | 6/2009 | Lifshitz et al. |
| 2009/0168960 A1 | 7/2009 | Jongen et al. |
| 2009/0202045 A1 | 8/2009 | Guertin et al. |
| 2009/0217456 A1 | 9/2009 | Lempen et al. |
| 2009/0260636 A1 | 10/2009 | Markstroem |
| 2009/0261275 A1 | 10/2009 | Rietzel |
| 2009/0296885 A1 | 12/2009 | Boeh |
| 2009/0299634 A1 | 12/2009 | Schaffner |
| 2009/0304153 A1 | 12/2009 | Amelia et al. |
| 2009/0304154 A1 | 12/2009 | Lomax et al. |
| 2009/0309046 A1 | 12/2009 | Balakin |
| 2009/0314960 A1 | 12/2009 | Balakin |

FOREIGN PATENT DOCUMENTS

| | | |
|---|---|---|
| DE | 2833800 | 12/1979 |
| DE | 3643893 | 6/1988 |
| DE | 4418216 | 11/1995 |
| DE | 19612091 | 3/1997 |
| DE | 102005034912 | 2/2007 |
| EP | 019136 | 11/1980 |
| EP | 247449 | 12/1987 |
| EP | 283082 | 9/1988 |
| EP | 465590 | 1/1992 |
| EP | 480035 | 4/1992 |
| EP | 809525 | 12/1997 |
| EP | 986070 | 3/2000 |
| EP | 986071 | 3/2000 |
| EP | 1064881 | 1/2001 |
| EP | 1454653 | 9/2004 |
| EP | 1584353 | 10/2005 |
| EP | 1585578 | 10/2005 |
| EP | 1709994 | 10/2006 |
| EP | 1792595 | 6/2007 |
| EP | 1795229 | 6/2007 |
| EP | 1900392 | 3/2008 |
| EP | 1935453 | 6/2008 |
| EP | 2108402 | 10/2009 |
| EP | 2116277 | 11/2009 |
| FR | 2701391 | 8/1994 |
| GB | 0870225 | 6/1961 |

| | | |
|---|---|---|
| GB | 1362678 | 8/1974 |
| GB | 2213066 | 8/1989 |
| GB | 2254691 | 10/1992 |
| JP | 61194400 | 8/1986 |
| JP | 03-94736 | 4/1991 |
| JP | 4-339282 | 11/1992 |
| JP | 7-204184 | 8/1995 |
| JP | 2003-527763 | 9/2003 |
| NL | 7309246 | 10/1974 |
| WO | WO 88/01848 | 3/1988 |
| WO | WO 90/11721 | 10/1990 |
| WO | WO 90/11723 | 10/1990 |
| WO | WO 96/25200 | 8/1996 |
| WO | WO 99/10137 | 3/1999 |
| WO | WO 00/59575 | 10/2000 |
| WO | WO 01/00276 | 1/2001 |
| WO | WO 01/89625 | 11/2001 |
| WO | WO 02/45793 | 6/2002 |
| WO | WO 03/039212 | 5/2003 |
| WO | WO 03/053520 | 7/2003 |
| WO | WO 03/076016 | 9/2003 |
| WO | WO2004/026401 | 4/2004 |
| WO | WO 2004/032781 | 4/2004 |
| WO | WO 2004/060486 | 7/2004 |
| WO | WO 2005/018734 | 3/2005 |
| WO | WO 2005/018735 | 3/2005 |
| WO | WO 05/037167 | 4/2005 |
| WO | WO 2005/102453 | 11/2005 |
| WO | WO 2006/060886 | 6/2006 |
| WO | WO 2006/076545 | 7/2006 |
| WO | WO 2006/094533 | 9/2006 |
| WO | WO 2007/012646 | 2/2007 |
| WO | WO 2007/016022 | 2/2007 |
| WO | WO 2007/054140 | 5/2007 |
| WO | WO 2007/061426 | 5/2007 |
| WO | WO 2007/062788 | 6/2007 |
| WO | WO 2007/068066 | 6/2007 |
| WO | WO 2007/127970 | 11/2007 |
| WO | WO 2008/003526 | 1/2008 |
| WO | WO 2008/051358 | 5/2008 |
| WO | WO 2008/064271 | 5/2008 |
| WO | WO 2008/081480 | 7/2008 |
| WO | WO 2008/142695 | 11/2008 |
| WO | WO 2009/129847 | 10/2009 |
| WO | WO 98/52646 | 11/2009 |
| WO | WO 2009/135879 | 11/2009 |
| WO | WO 2009/142544 | 11/2009 |
| WO | WO 2009/142545 | 11/2009 |
| WO | WO 2009/142546 | 11/2009 |
| WO | WO 2009/142547 | 11/2009 |
| WO | WO 2009/142548 | 11/2009 |
| WO | WO 2009/142549 | 11/2009 |

OTHER PUBLICATIONS

"Design of a Proton Therapy Synchrotron" by Fermi National Accelerator Laboratory, Jun. 1986, LL467-LL574.

"Proceedings of a Medical Workshop on Accelerators for Charged-Particle Beam Therapy" by Fermilab, Jan. 1985, LL33170-LL33313.

"Product Overview" by BrainLAB Radiotherapy Solutions, Copyright 2004 BrainLAB AG.

"Proton Therapy Facility: Engineering Design Report" by Fermi National Accelerator Laboratory, Feb. 1987, LL45441-LL45570.

"Proton Therapy System" by Brobeck Corporation, Nov. 1985, LL54413-LL54459.

European Search Report for Application No. 02789303.1, dated Dec. 3, 2004.

International Search Report for PCT/US02/34556, dated Apr. 2, 2003.

Matsu'Ura, Jun, "Systems for Overall Control and Beam Transport of the Himac," Mitsubishi Electric Advance, Mitsubishi Electric Corporation, Tokyo, JP, vol. 72, Sep. 1995, pp. 5-7.

R.A. Gough, E.L. Alpen, "The Heavy Ion Medical Accelerator - Final Design Summary", Pub 5122, Jun. 1984, Lawrence Berkeley Laboratory, University of California, Berkeley, CA 94720.

K. Lipinski, "Lexikon der Datenkommunikation", Bergheim, Datacom, 3rd Edition, 1995, ISBN 3-89238-123-2, particularly p. 18, p. 96, p. 97, p. 411.

* cited by examiner

PATH PLANNING AND COLLISION AVOIDANCE FOR MOVEMENT OF INSTRUMENTS IN A RADIATION THERAPY ENVIRONMENT

RELATED APPLICATIONS

This application is a continuation of U.S. patent application Ser. No. 10/917,220, filed Aug. 12, 2004, and claims the benefit of the U.S. Provisional Application No. 60/494,699 filed Aug. 12, 2003 and U.S. Provisional Application No. 60/579,095 filed Jun. 10, 2004 both entitled "Precision Patient Alignment and Beam Therapy System" and all of which are incorporated in their entireties herein by reference.

GOVERNMENT SUPPORT

This invention was made with United States Government support under the DAMD17-99-1-9477 and DAMD17-02-1-0205 grants awarded by the Department of Defense. The Government has certain rights in the invention.

BACKGROUND OF THE INVENTION

1. Field of the Invention

The invention relates to the field of radiation therapy systems. One embodiment includes an active path planning and collision avoidance system to facilitate movement of objects in a radiation therapy environment in an efficient manner and so as to proactively avoid possible collisions.

2. Description of the Related Art

Radiation therapy systems are known and used to provide treatment to patients suffering a wide variety of conditions. Radiation therapy is typically used to kill or inhibit the growth of undesired tissue, such as cancerous tissue. A determined quantity of high-energy electromagnetic radiation and/or high-energy particles are directed into the undesired tissue with the goal of damaging the undesired tissue while reducing unintentional damage to desired or healthy tissue through which the radiation passes on its path to the undesired tissue.

Proton therapy has emerged as a particularly efficacious treatment for a variety of conditions. In proton therapy, positively charged proton subatomic particles are accelerated, collimated into a tightly focused beam, and directed towards a designated target region within the patient. Protons exhibit less lateral dispersion upon impact with patient tissue than electromagnetic radiation or low mass electron charged particles and can thus be more precisely aimed and delivered along a beam axis. Also, upon impact with patient tissue, protons exhibit a characteristic Bragg peak wherein a significant portion of the kinetic energy of the accelerated mass is deposited within a relatively narrow penetration depth within the patient. This offers the significant advantage of reducing delivery of energy from the accelerated proton particles to healthy tissue interposed between the target region and the delivery nozzle of a proton therapy machine as well as to "downrange" tissue lying beyond the designated target region. Depending on the indications for a particular patient and their condition, delivery of the therapeutic proton beam may preferably take place from a plurality of directions in multiple treatment fractions to maintain a total dose delivered to the target region while reducing collateral exposure of interposed desired/healthy tissue.

Thus, a radiation therapy system, such as a proton beam therapy system, typically has provision for positioning a patient with respect to a proton beam in multiple orientations. In order to determine a preferred aiming point for the proton beam within the patient, the typical procedure has been to perform a computed tomography (CT) scan in an initial planning or prescription stage from which multiple digitally reconstructed radiographs (DRRs) can be determined. The DRRs synthetically represent the three dimensional data representative of the internal physiological structure of the patient obtained from the CT scan in two dimensional views considered from multiple orientations. A desired target isocenter corresponding to the tissue to which therapy is to be provided is designated. The spatial location of the target isocenter can be referenced with respect to physiological structure of the patient (monuments) as indicated in the DRRs.

Upon subsequent setup for delivery of the radiation therapy, an x-ray imager is moved into an imaging position and a radiographic image is taken of the patient. This radiographic image is compared or registered with the DRRs with respect to the designated target isocenter. The patient's position is adjusted to, as closely as possible, align the target isocenter in a desired pose with respect to the radiation beam as indicated by the physician's prescription. The desired pose is frequently chosen as that of the initial planning or prescription scan. Depending on the particular application, either the patient and/or the beam nozzle will need to be moved.

There is a desire that movement of components of the therapy system to achieve alignment be done in an accurate, rapid manner while maintaining overall system safety. In particular, a radiation therapy apparatus is an expensive piece of medical equipment to construct and maintain both because of the materials and equipment needed in construction and the indication for relatively highly trained personnel to operate and maintain the apparatus. In addition, radiation therapy, such as proton therapy, is increasing being found an effective treatment for a variety of patient conditions and thus it is desirable to increase patient throughput both to expand the availability of this beneficial treatment to more patients in need of the same as well as reducing the end costs to the patients or insurance companies paying for the treatment and increase the profitability for the therapy delivery providers. As the actual delivery of the radiation dose, once the patient is properly positioned, is relatively quick, any additional latency in patient ingress and egress from the therapy apparatus, imaging, and patient positioning and registration detracts from the overall patient throughput and thus the availability, costs, and profitability of the system.

The movable components of a radiation therapy system also tend to be rather large and massive, thus indicating powered movement of the various components. As the components tend to have significant inertia during movement and are typically power driven, a safety system to inhibit damage and injury can be provided. Safety systems can include power interrupts based on contact switches. The contact switches are activated at motion stop range of motion limits to cut power to drive motors. Hard motion stops or limiters can also be provided to physically impede movement beyond a set range. However, contact switches and hard stops are activated when the corresponding component(s) reach the motion limit and thus impose a relatively abrupt motion stop which adds to wear on the machinery and can even lead to damage if engaged excessively. In addition, particularly in application involving multiple moving components, a motion stop arrangement of contact switches and/or hard limiters involves significant complexity to inhibit collision between the multiple components and can lead to inefficiencies in the overall system operation if the components are limited to moving one at a time to simplify the collision avoidance.

From the foregoing it will be understood that there is a need for providing a collision avoidance system to maintain operating safety and damage control while positioning multiple movable components of a radiation therapy delivery system. There is also a desire to maintain the accuracy and speed of the patient registration process when implementing such a collision avoidance system.

SUMMARY OF THE INVENTION

Embodiments of the invention provide a patient positioning system for a therapeutic radiation system having moving components. The patient positioning system pre-plans and analyzes movements to increase movement efficiency for decreased latency and to pro-actively avoid collisions. The patient positioning system includes multiple cameras that can both determine the location of fixed and movable components of the system as well as monitor for possible intrusion into a movement path of a foreign object or personnel. The system provides significant safety advantages over systems employing motion stops.

One embodiment comprises a radiation therapy delivery system having fixed and movable components, the system comprising a gantry, a patient pod configured to secure a patient substantially immobile with respect to the patient pod, a patient positioner interconnected to the patient pod so as to position the patient pod along multiple translational and rotational axes within the gantry, a radiation therapy nozzle interconnected to the gantry and selectively delivering radiation therapy along a beam axis, a plurality of external measurement devices which obtain position measurements of at least the patient pod and nozzle, and a controller which receives the position measurements of at least the patient pod and nozzle and determines movement commands to position the patient in a desired pose with respect to the beam axis and corresponding movement trajectories of the patient pod with respect to other fixed and movable components of the therapy delivery system based upon the movement commands and determines whether a collision is indicated for the movement commands and inhibits movement if a collision would be indicated.

Another embodiment comprises a path planning and collision avoidance system for a radiation therapy system having fixed and movable components and selectively delivering a radiation therapy beam along a beam axis, the positioning system comprising a plurality of external measurement devices arranged to obtain position measurements of the components so as to provide location information, a movable patient support configured to support a patient substantially fixed in position with respect to the patient support and controllably position the patient in multiple translational and rotational axes, and a controller receiving position information from the plurality of external measurement devices and providing movement commands to the movable patient support to automatically align the patient in a desired pose and determining a corresponding movement envelope wherein the controller evaluates the movement envelope and inhibits movement of the patient support if a collision is indicated else initiates the movement.

A further embodiment comprises a method of registering and positioning a patient for delivery of therapy with a system having fixed and at least one movable components, the method comprising the steps of positioning a patient in an initial treatment pose with a controllable patient positioner, externally measuring the location of selected points of the fixed and at least one movable components, determining a difference vector between the observed initial patient pose and a desired patient pose, determining corresponding movement commands and a movement trajectory for the patient positioner to bring the patient to the desired patient pose, and comparing the movement trajectory with the measured locations of the selected points of the fixed and at least one movable components so as to inhibit movement of the patient positioner if a collision is indicated.

Yet another embodiment comprises a system for delivering radiation therapy to a pre-selected location within a patient, the system comprising a plurality of movable components including a patient positioner and a nozzle, the system further comprising an external monitoring system that monitors the physical location of the plurality of movable components and provides signals indicative thereof and wherein the system further includes internal monitoring systems that also monitor the movement of the plurality of movable components and provides signals indicative thereof and wherein the system monitors the signals from the external and internal monitoring systems and inhibits movement of the plurality of components if the signals indicate that a collision of components is likely to occur.

These and other objects and advantages of the invention will become more apparent from the following description taken in conjunction with the accompanying drawings.

BRIEF DESCRIPTION OF THE DRAWINGS

A schematic diagram of one embodiment of a radiation therapy system with a patient positioning system in a first orientation is shown in FIG. 1A and in a second orientation in FIG. 1B.

DETAILED DESCRIPTION OF THE PREFERRED EMBODIMENT

Figure 1A:
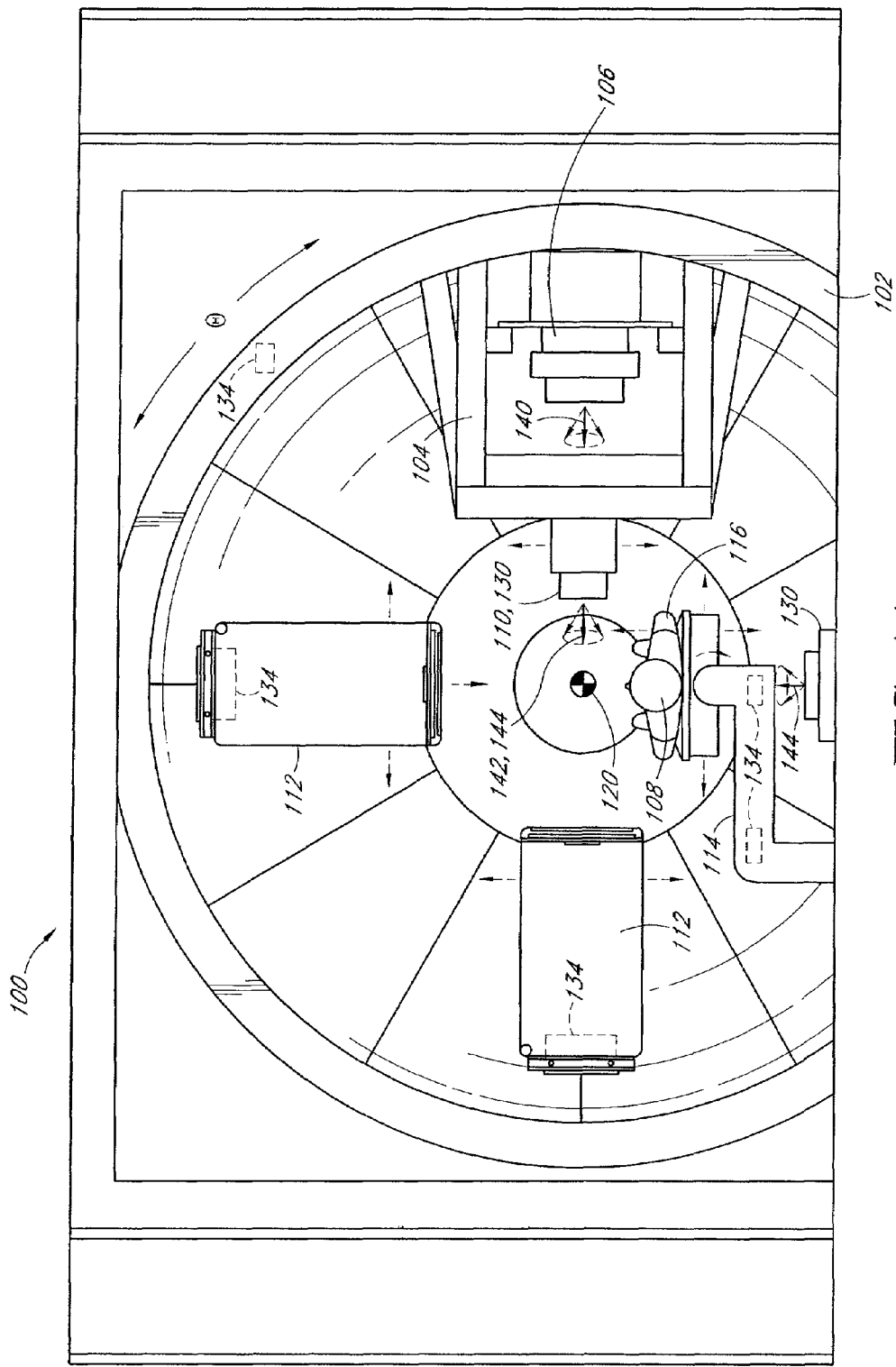
Figure 1B:
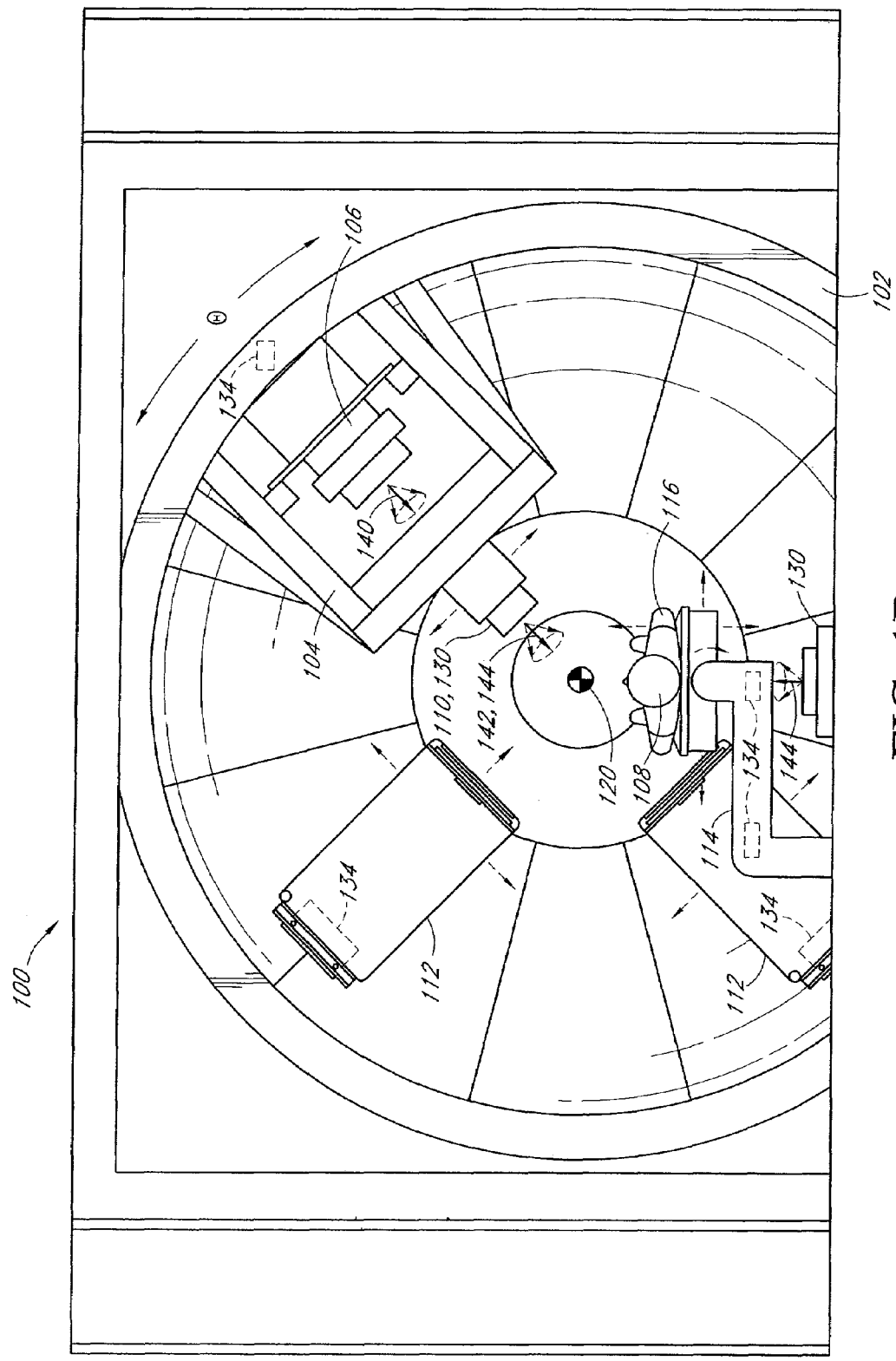

Reference will now be made to the drawings wherein like reference designators refer to like parts throughout. FIGS. 1A and 1B illustrate schematically first and second orientations of one embodiment of a radiation therapy system 100, such as based on the proton therapy system currently in use at Loma Linda University Medical Center in Loma Linda, Calif. and as described in U.S. Pat. No. 4,870,287 of Sep. 26, 1989 which is incorporated herein in its entirety by reference. The radiation therapy system 100 is designed to deliver therapeutic radiation doses to a target region within a patient for treatment of malignancies or other conditions from one or more angles or orientations with respect to the patient. The system 100 includes a gantry 102 which includes a generally hemispherical or frustoconical support frame for attachment and support of other components of the radiation therapy system 100. Additional details on the structure and operation of embodiments of the gantry 102 may be found in U.S. Pat. Nos. 4,917,344 and 5,039,057, both of which are incorporated herein in their entirety by reference.

The system 100 also comprises a nozzle 104 which is attached and supported by the gantry 102 such that the gantry 102 and nozzle 104 may revolve relatively precisely about a gantry isocenter 120, but subject to corkscrew, sag, and other distortions from nominal. The system 100 also comprises a radiation source 106 delivering a radiation beam along a radiation beam axis 140, such as a beam of accelerated protons. The radiation beam passes through and is shaped by an aperture 110 to define a therapeutic beam delivered along a delivery axis 142. The aperture 110 is positioned on the distal end of the nozzle 104 and the aperture 110 may preferably be specifically configured for a patient's particular prescription of therapeutic radiation therapy. In certain applications, multiple apertures 110 are provided for different treatment fractions.

Figure 2B:
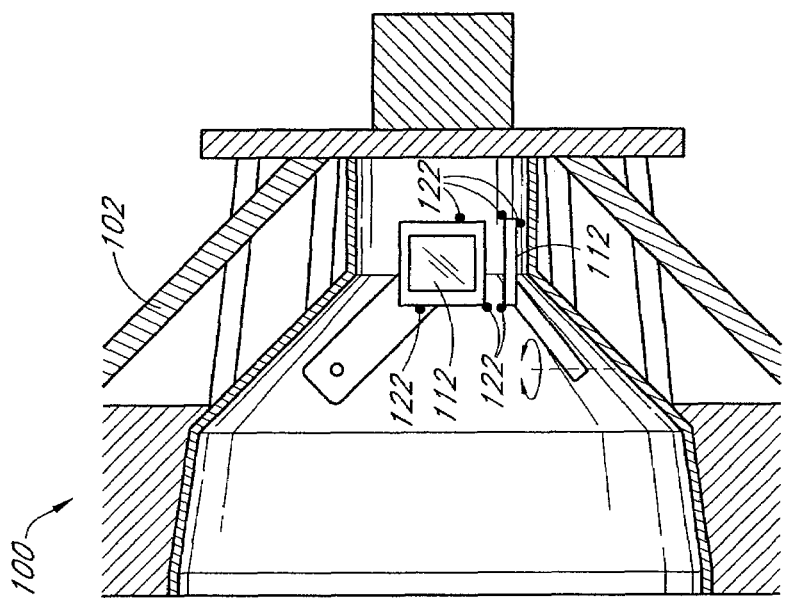
FIG. 2A illustrates one embodiment of retractable imagers in an extended position and FIG. 2B illustrates the imagers in a retracted position.
Figure 2A:
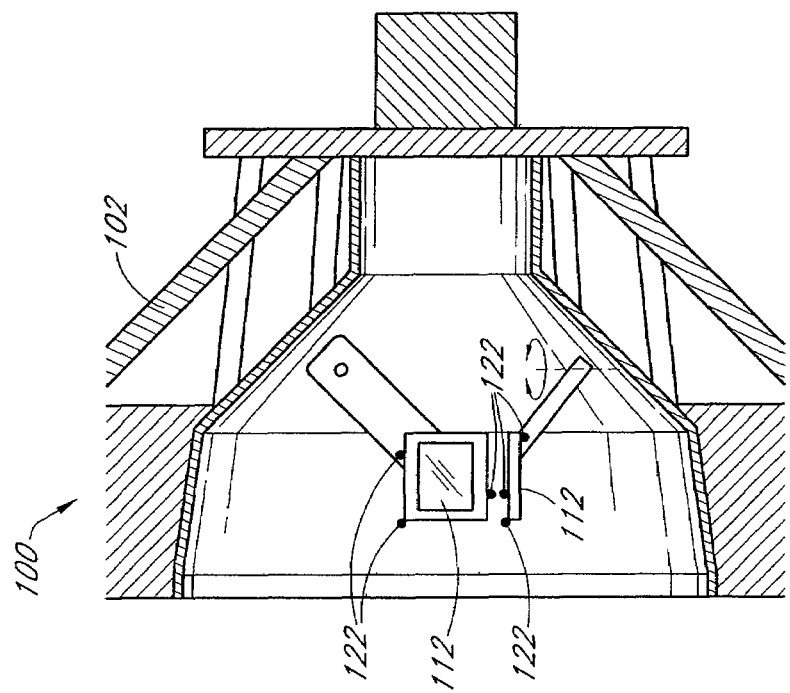

The system 100 also comprises one or more imagers 112 which, in this embodiment, are retractable with respect to the gantry 102 between an extended position as illustrated in FIG. 2A and a retracted position as illustrated in FIG. 2B. The imager 112 in one implementation comprises a commercially available solid-state amorphous silicon x-ray imager which can develop image information such as from incident x-ray radiation that has passed through a patient's body. The retractable aspect of the imager 112 provides the advantage of withdrawing the imager screen from the delivery axis 142 of the radiation source 106 when the imager 112 is not needed thereby providing additional clearance within the gantry 102 enclosure as well as placing the imager 112 out of the path of potentially harmful emissions from the radiation source 106 thereby reducing the need for shielding to be provided to the imager 112.

The system 100 also comprises corresponding one or more x-ray sources 130 which selectively emit appropriate x-ray radiation along one or more x-ray source axes 144 so as to pass through interposed patient tissue to generate a radiographic image of the interposed materials via the imager 112. The particular energy, dose, duration, and other exposure parameters preferably employed by the x-ray source(s) 130 for imaging and the radiation source 106 for therapy will vary in different applications and will be readily understood and determined by one of ordinary skill in the art.

In this embodiment, at least one of the x-ray sources 130 is positionable such that the x-ray source axis 144 can be positioned so as to be nominally coincident with the delivery axis 142. This embodiment provides the advantage of developing a patient image for registration from a perspective which is nominally identical to a treatment perspective. This embodiment also includes the aspect that a first imager 112 and x-ray source 130 pair and a second imager 112 and x-ray source 130 pair are arranged substantially orthogonal to each other. This embodiment provides the advantage of being able to obtain patient images in two orthogonal perspectives to increase registration accuracy as will be described in greater detail below. The imaging system can be similar to the systems described in U.S. Pat. Nos. 5,825,845 and 5,117,829 which are hereby incorporated by reference.

Figure 3:
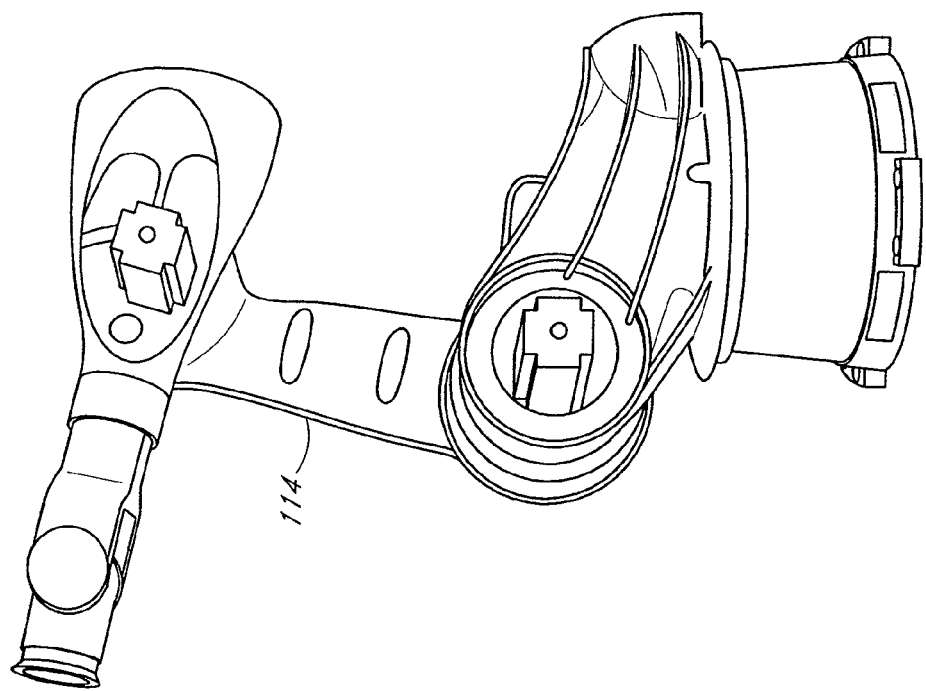
FIG. 3 illustrates one embodiment of a patient positioner to which a patient pod can be attached.

The system 100 also comprises a patient positioner 114 (FIG. 3) and a patient pod 116 which is attached to a distal or working end of the patient positioner 114. The patient positioner 114 is adapted to, upon receipt of appropriate movement commands, position the patient pod 116 in multiple translational and rotational axes and preferably is capable of positioning the patient pod 116 in three orthogonal translational axes as well as three orthogonal rotational axes so as to provide a full six degree freedom of motion to placement of the patient pod 116.

The patient pod 116 is configured to hold a patient securely in place in the patient pod 116 so to as substantially inhibit any relative movement of the patient with respect to the patient pod 116. In various embodiments, the patient pod 116 comprises expandable foam, bite blocks, and/or fitted facemasks as immobilizing devices and/or materials. The patient pod 116 is also preferably configured to reduce difficulties encountered when a treatment fraction indicates delivery at an edge or transition region of the patient pod 116. Additional details of preferred embodiments of the patient positioner 114 and patient pod 116 can be found in the commonly assigned application Ser. No. 10/917,022, now U.S. Pat. No. 7,173,265, issued on Feb. 6, 2007 entitled "Modular Patient Support System" filed concurrently herewith and which is incorporated herein in its entirety by reference.

As previously mentioned, in certain applications of the system 100, accurate relative positioning and orientation of the therapeutic beam delivery axis 142 provided by the radiation source 106 with target tissue within the patient as supported by the patient pod 116 and patient positioner 114 is an important goal of the system 100, such as when comprising a proton beam therapy system. However, as previously mentioned, the various components of the system 100, such as the gantry 102, the nozzle 104, radiation source 106, the imager (s) 112, the patient positioner 114, the patient pod 116, and x-ray source(s) 130 are subject to certain amounts of structural flex and movement tolerances from a nominal position and orientation which can affect accurate delivery of the beam to that patient.

FIGS. 1A and 1B illustrate different arrangements of certain components of the system 100 and indicate by the broken arrows both translational and rotational deviations from nominal that can occur in the system 100. For example, in the embodiment shown in FIG. 1A, the nozzle 104 and first imager 112 extend substantially horizontally and are subject to bending due to gravity, particularly at their respective distal ends. The second imager 112 is arranged substantially vertically and is not subject to the horizontal bending of the first imager 112. FIG. 1B illustrates the system 100 in a different arrangement rotated approximately 45° counterclockwise from the orientation of FIG. 1A. In this orientation, both of the imagers 112 as well as the nozzle 104 are subject to bending under gravity, but to a different degree than in the orientation illustrated in FIG. 1A. The movement of the gantry 102 between different orientations, such as is illustrated in FIGS. 1A and 1B also subjects components of the system 100 to mechanical tolerances at the moving surfaces. As these deviations from nominal are at least partially unpredictable, non-repeatable, and additive, correcting for the deviations on a predictive basis is extremely challenging and limits overall alignment accuracy. It will be appreciated that these deviations from the nominal orientation of the system are simply exemplary and that any of a number of sources of error can be addressed by the system disclosed herein without departing from the spirit of the present invention.

FIGS. 4A-4E illustrate in greater detail embodiments of potential uncertainties or errors which can present themselves upon procedures for alignment of, for example, the nozzle 104 and the target tissue of the patient at an isocenter 120. FIGS. 4A-4E illustrate these sources of uncertainty or error with reference to certain distances and positions. It will be appreciated that the sources of error described are simply illustrative of the types of errors addressed by the system 100 of the illustrated embodiments and that the system 100 described is capable of addressing additional errors. In this embodiment, a distance SAD is defined as a source to axis distance from the radiation source 106 to the rotation axis of the gantry, which ideally passes through the isocenter 120. For purposes of explanation and appreciation of relative scale and distances, in this embodiment, SAD is approximately equal to 2.3 meters.

Figure 4A:
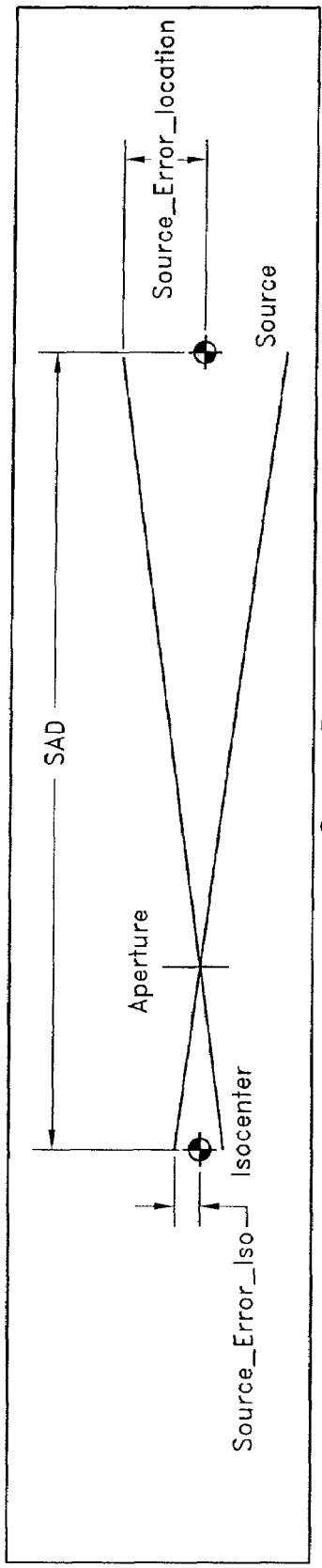
FIGS. 4A-4E illustrate various position error sources of one embodiment of a radiation therapy system.

FIG. 4A illustrates that one of the potential sources of error is a source error where the true location of the radiation source 106 is subject to offset from a presumed or nominal location. In this embodiment, the therapeutic radiation beam as provided by the radiation source 106 passes through two transmission ion chambers (TIC) which serve to center the beam. These are indicated as TIC 1 and TIC 3 and these are also affixed to the nozzle 104. The source error can arise from numerous sources including movement of the beam as observed on TIC 1 and/or TIC 3, error in the true gantry 102 rotational angle, and error due to "egging" or distortion from round of the gantry 102 as it rotates. FIG. 4A illustrates source error comprising an offset of the true position of the radiation source 106 from a presumed or nominal location and the propagation of the radiation beam across the SAD distance through the aperture 110 providing a corresponding error at isocenter 120.

Figure 4B:
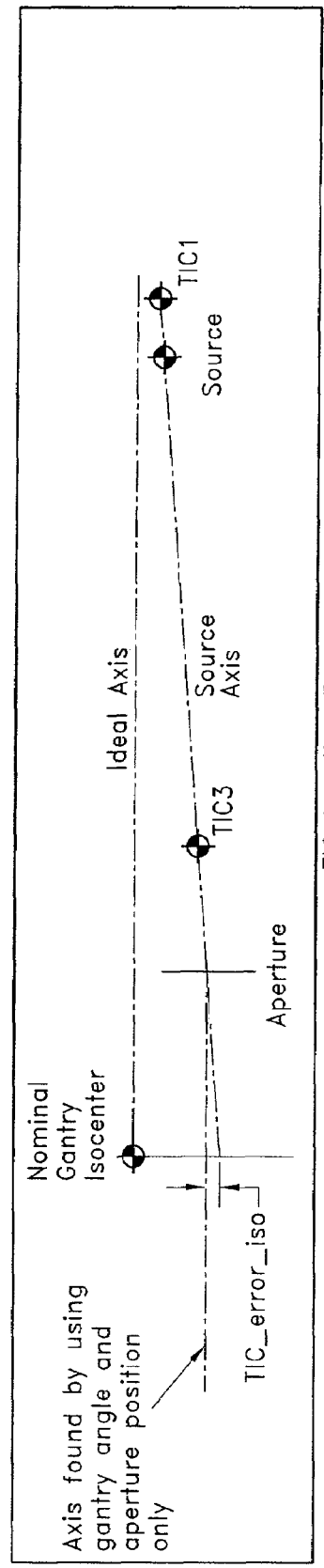

FIG. 4B illustrates possible error caused by TIC location error, where TIC 1, the radiation source 106, and TIC 3 are offset from an ideal beam axis passing through the nominal gantry isocenter 120. As the errors illustrated by FIGS. 4A and 4B are assumed random and uncorrelated, they can be combined in quadrature and projected through an assumed nominal center of the aperture 110 to establish a total error contribution due to radiation source 106 error projected to the isocenter 120. In this embodiment, before corrective measures are taken (as described in greater detail below), the radiation source error can range from approximately ±0.6 mm to ±0.4 mm.

Figure 4C:
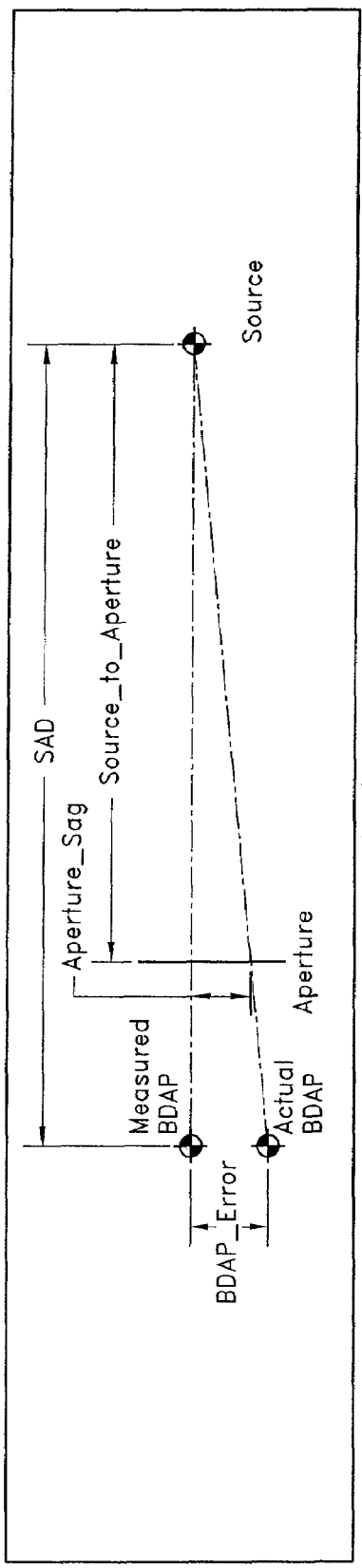

FIG. 4C illustrates error or uncertainty due to position of the aperture 110. The location of the radiation source 106 is assumed nominal; however, error or uncertainty is introduced both by tolerance stack-up, skew, and flex of the nozzle 104 as well as manufacturing tolerances of the aperture 110 itself. Again, as projected from the radiation source 106 across the distance SAD to the nominal isocenter 120, a beam delivery aiming point (BDAP) error is possible between a presumed nominal BDAP and an actual BDAP. In this embodiment, this BDAP error arising from error in the aperture 110 location ranges from approximately ±1.1 mm to ±1.5 mm.

Figure 4D:
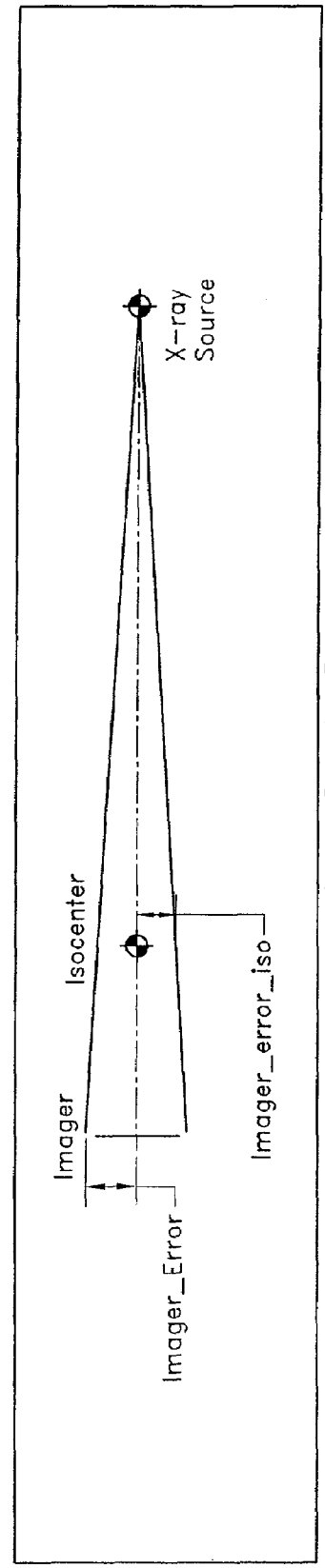
Figure 4E:
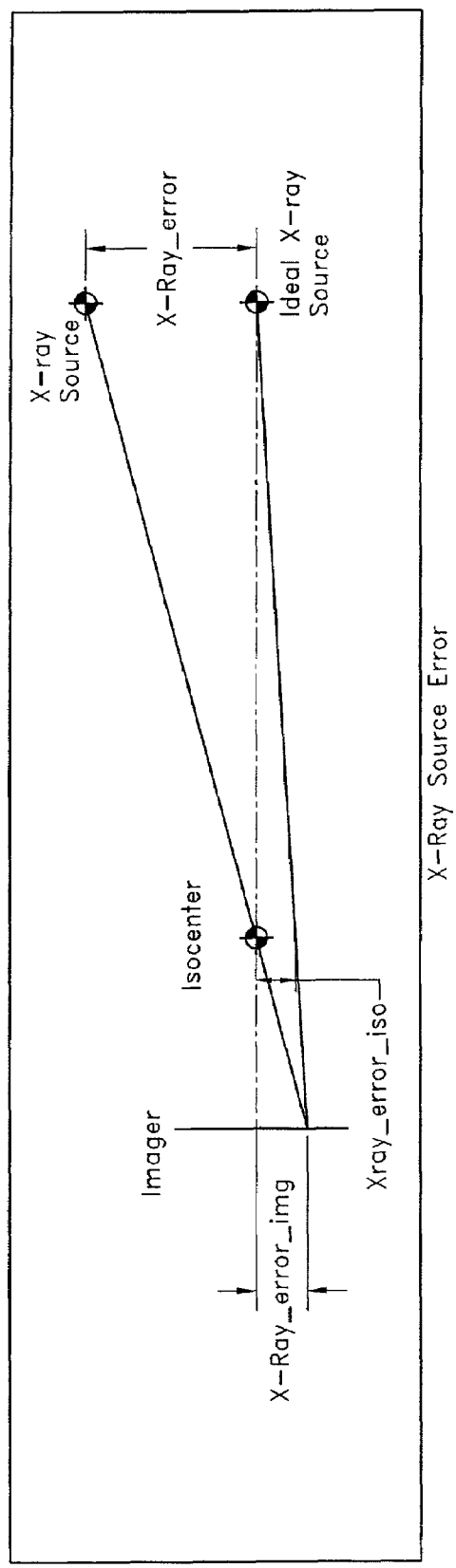

The system 100 is also subject to error due to positioning of the imager(s) 112 as well as the x-ray source(s) 130 as illustrated in FIGS. 4D and 4E. FIG. 4D illustrates the error due to uncertainty in the imager(s) 112 position with the position of the corresponding x-ray source(s) 130 assumed nominal. As the emissions from the x-ray source 130 pass through the patient assumed located substantially at isocenter 120 and onward to the imager 112, this distance may be different than the SAD distance and in this embodiment is approximately equal to 2.2 meters. Error or uncertainty in the true position of an imager 112 can arise from lateral shifts in the true position of the imager 112, errors due to axial shifting of the imager 112 with respect to the corresponding x-ray source 130, as well as errors in registration of images obtained by imager 112 to the DRRs. In this embodiment, before correction, the errors due to each imager 112 are approximately ±0.7 mm.

Similarly, FIG. 4E illustrates errors due to uncertainty in positioning of the x-ray source(s) 130 with the position of the corresponding imager(s) 112 assumed nominal. Possible sources of error due to the x-ray source 130 include errors due to initial alignment of the x-ray source 130, errors arising from movement of the x-ray source 130 into and out of the beam line, and errors due to interpretation of sags and relative distances of TIC 1 and TIC 3. These errors are also assumed random and uncorrelated or independent and are thus added in quadrature resulting, in this embodiment, in error due to each x-ray source 130 of approximately ±0.7 mm.

As these errors are random and independent and uncorrelated and thus potentially additive, in this embodiment the system 100 also comprises a plurality of external measurement devices 124 to evaluate and facilitate compensating for these errors. In one embodiment, the system 100 also comprises monuments, such as markers 122, cooperating with the external measurement devices 124 as shown in FIGS. 2A, 2B, 6 and 7. The external measurement devices 124 each obtain measurement information about the three-dimensional position in space of one or more components of the system 100 as indicated by the monuments as well as one or more fixed landmarks 132 also referred to herein as the "world" 132.

In this embodiment, the external measurement devices 124 comprise commercially available cameras, such as CMOS digital cameras with megapixel resolution and frame rates of 200-1000 Hz, which independently obtain optical images of objects within a field of view 126, which in this embodiment is approximately 85° horizontally and 70° vertically. The external measurement devices 124 comprising digital cameras are commercially available, for example as components of the Vicon Tracker system from Vicon Motion Systems Inc. of Lake Forrest, Calif. However, in other embodiments, the external measurement devices 124 can comprise laser measurement devices and/or radio location devices in addition to or as an alternative to the optical cameras of this embodiment.

In this embodiment, the markers 122 comprise spherical, highly reflective landmarks which are fixed to various components of the system 100. In this embodiment, at least three markers 122 are fixed to each component of the system 100 of interest and are preferably placed asymmetrically, e.g. not equidistant from a centerline nor evenly on corners, about the object. The external measurement devices 124 are arranged such that at least two external measurement devices 124 have a given component of the system 100 and the corresponding markers 122 in their field of view and in one embodiment a total of ten external measurement devices 124 are provided. This aspect provides the ability to provide binocular vision to the system 100 to enable the system 100 to more accurately determine the location and orientation of components of the system 100. The markers 122 are provided to facilitate recognition and precise determination of the position and orientation of the objects to which the markers 122 are affixed, however in other embodiments, the system 100 employs the external measurement devices 124 to obtain position information based on monuments comprising characteristic outer contours of objects, such as edges or corners, comprising the system 100 without use of the external markers 122.

Figure 5:
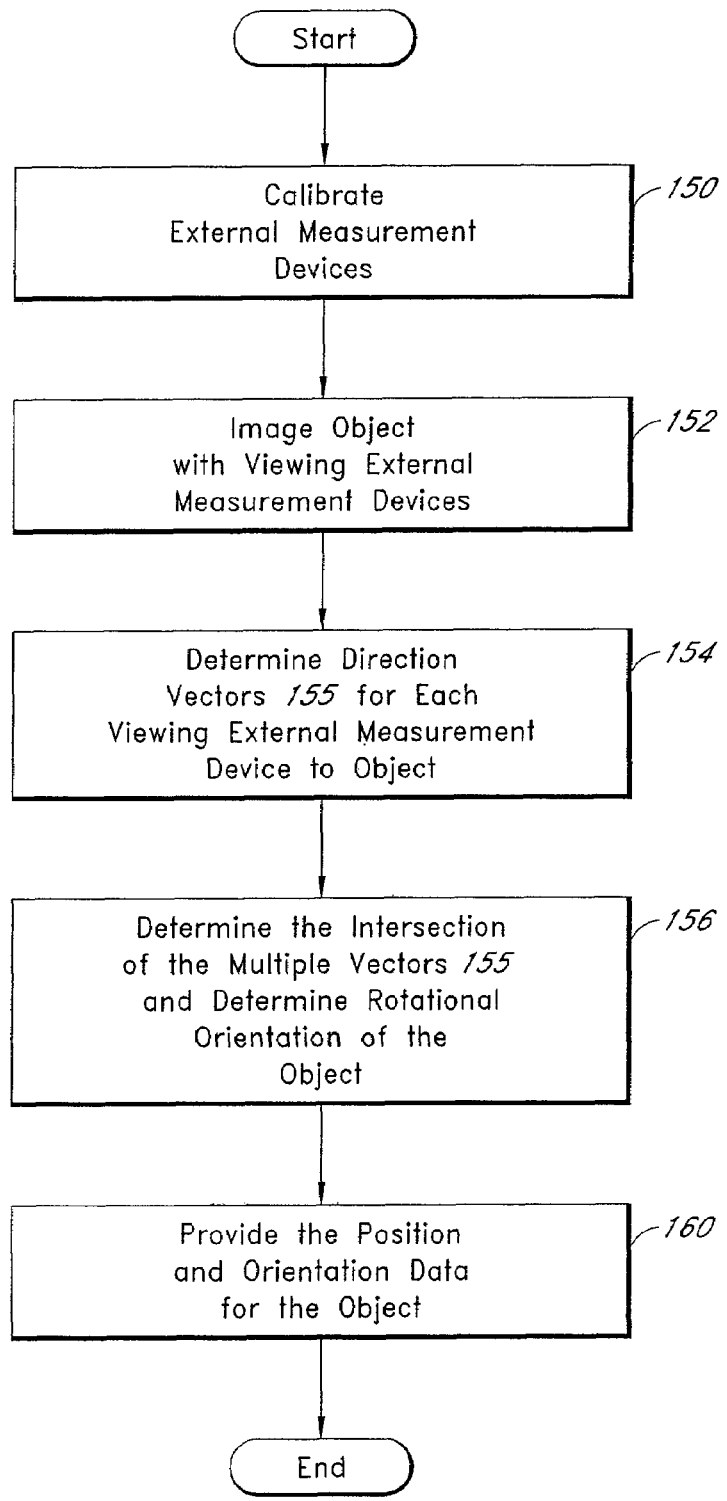
FIG. 5 is a flow chart of one embodiment of a method of determining the position and orientation of objects in a radiation therapy environment.

FIG. 5 illustrates one embodiment of determining the spatial position and angular orientation of a component of the system 100. As the component(s) of interest can be the gantry 102, nozzle 104, aperture 110, imager 112, world 132 or other components, reference will be made to a generic "object". It will be appreciated that the process described for the object can proceed in parallel or in a series manner for multiple objects. Following a start state, in state 150 the system 100 calibrates the multiple external measurement devices 124 with respect to each other and the world 132. In the calibration state, the system 100 determines the spatial position and angular orientation of each external measurement device 124. The system 100 also determines the location of the world 132 which can be defined by a dedicated L-frame and can define a spatial origin or frame-of-reference of the system 100. The world 132 can, of course, comprise any component or structure that is substantially fixed within the field of view of the external measurement devices 124. Hence, structures that are not likely to move or deflect as a result of the system 100 can comprise the world 132 or point of reference for the external measurement devices 124.

A wand, which can include one or more markers 122 is moved within the fields of view 126 of the external measurement devices 124. As the external measurement devices 124 are arranged such that multiple external measurement devices 124 (in this embodiment at least two) have an object in the active area of the system 100 in their field of view 126 at any given time, the system 100 correlates the independently provided location and orientation information from each external measurement device 124 and determines corrective factors such that the multiple external measurement devices 124 provide independent location and orientation information that is in agreement following calibration. The particular mathematical steps to calibrate the external measurement devices 124 are dependent on their number, relative spacing, geometrical orientations to each other and the world 132, as well as the coordinate system used and can vary among particular applications, however will be understood by one of ordinary skill in the art. It will also be appreciated that in certain applications, the calibration state 150 would need to be repeated if one or more of the external measurement devices 124 or world 132 is moved following calibration.

Figure 6:
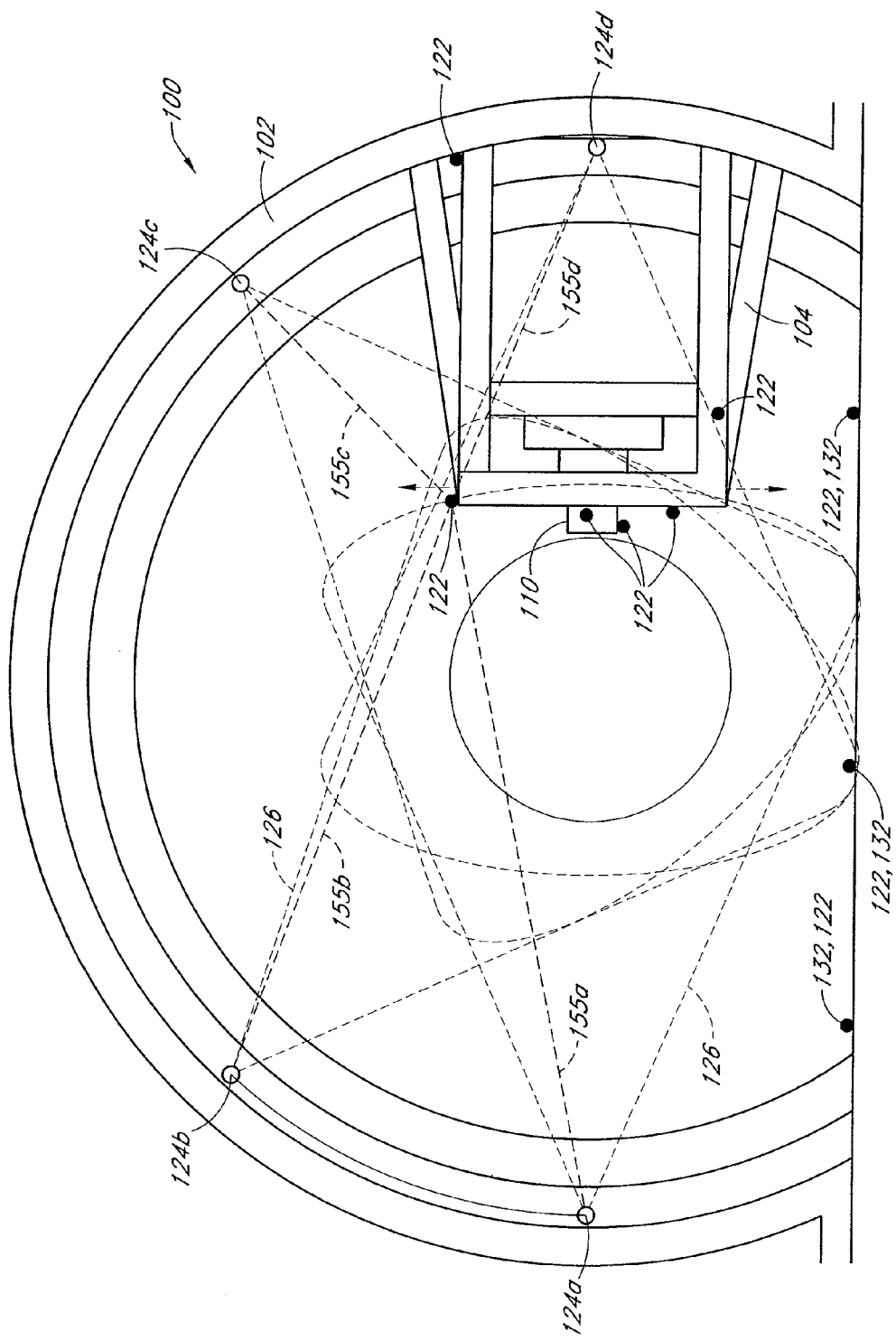
FIG. 6 illustrates one embodiment of external measurement devices for a radiation therapy system.
Figure 7:
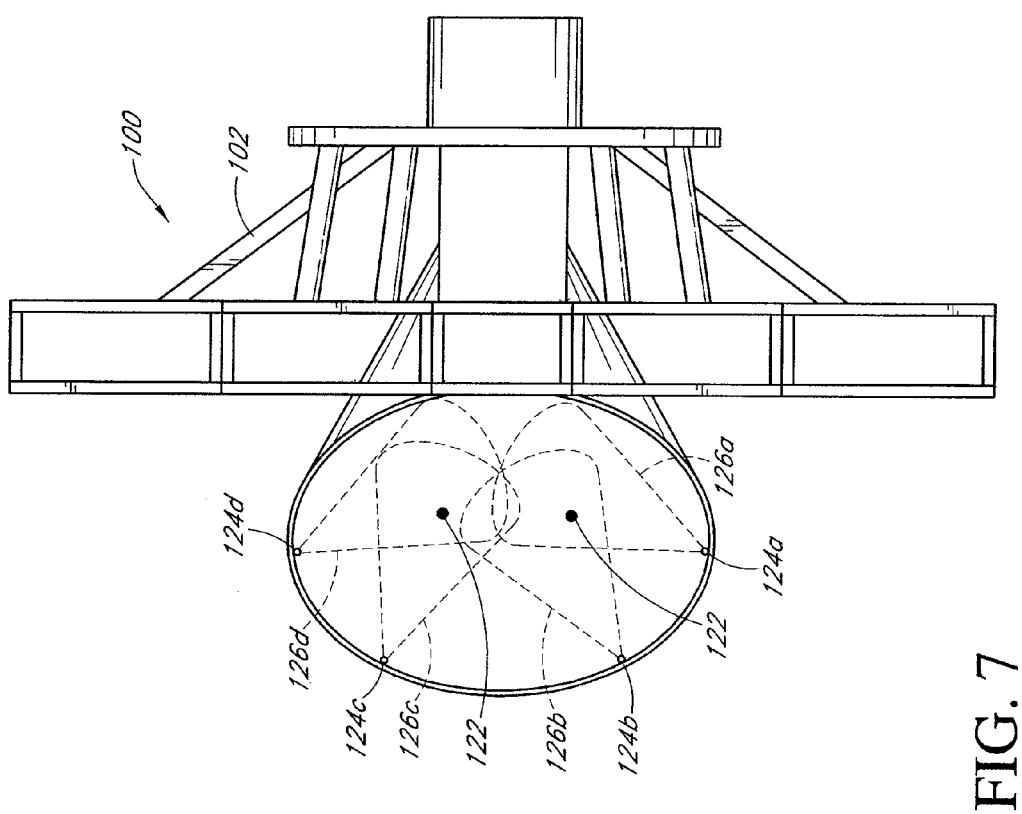
FIG. 7 illustrates further embodiments of external measurement devices for a radiation therapy system.

Following the calibration state 150, in state 152 multiple external measurement devices 124 obtain an image of the object(s) of interest. From the images obtained in state 152, the system 100 determines a corresponding direction vector 155 to the object from each corresponding external measurement device 124 which images the object in state 154. This is illustrated in FIG. 6 as vectors 155a-d corresponding to the external measurement devices 124a-d which have the object in their respective fields of view 126. Then, in state 156, the system 100 calculates the point in space where the vectors 155 (FIG. 6) determined in state 154 intersect. State 156 thus returns a three-dimensional location in space, with reference to the world 132, for the object corresponding to multiple vectors intersecting at the location. As the object has been provided with three or more movements or markers 122, the system 100 can also determine the three-dimensional angular orientation of the object by evaluating the relative locations of the individual markers 122 associated with the object. In this implementation, the external measurement devices 124 comprise cameras, however, any of a number of different devices can be used to image, e.g., determine the location, of the monuments without departing from the spirit of the present invention. In particular, devices that emit or receive electromagnetic or audio energy including visible and non-visible wavelength energy and ultra-sound can be used to image or determine the location of the monuments.

The location and orientation information determined for the object is provided in state 160 for use in the system 100 as described in greater detail below. In one embodiment, the calibration state 150 can be performed within approximately one minute and allows the system 100 to determine the object's location in states 152, 154, 156, and 160 to within 0.1 mm and orientation to within 0.15° with a latency of no more than 10 ms. As previously mentioned, in other embodiments, the external measurement devices 124 can comprise laser measurement devices, radio-location devices or other devices that can determine direction to or distance from the external measurement devices 124 in addition to or as an alternative to the external measurement devices 124 described above. Thus, in certain embodiments a single external measurement device 124 can determine both range and direction to the object to determine the object location and orientation. In other embodiments, the external measurement devices 124 provide only distance information to the object and the object's location in space is determined by determining the intersection of multiple virtual spheres centered on the corresponding external measurement devices 124.

In certain embodiments, the system 100 also comprises one or more local position feedback devices or resolvers 134 (See, e.g., FIG. 1). The local feedback devices or resolvers 134 are embodied within or in communication with one or more components of the system 100, such as the gantry 102, the nozzle 104, the radiation source 106, the aperture 110, the imager(s) 112, patient positioner 114, patient pod 116, and/or world 132. The local feedback devices 134 provide independent position information relating to the associated component of the system 100. In various embodiments, the local feedback devices 134 comprise rotary encoders, linear encoders, servos, or other position indicators that are commercially available and whose operation is well understood by one of ordinary skill in the art. The local feedback devices 134 provide independent position information that can be utilized by the system 100 in addition to the information provided by the external measurement devices 124 to more accurately position the patient.

Figure 8:
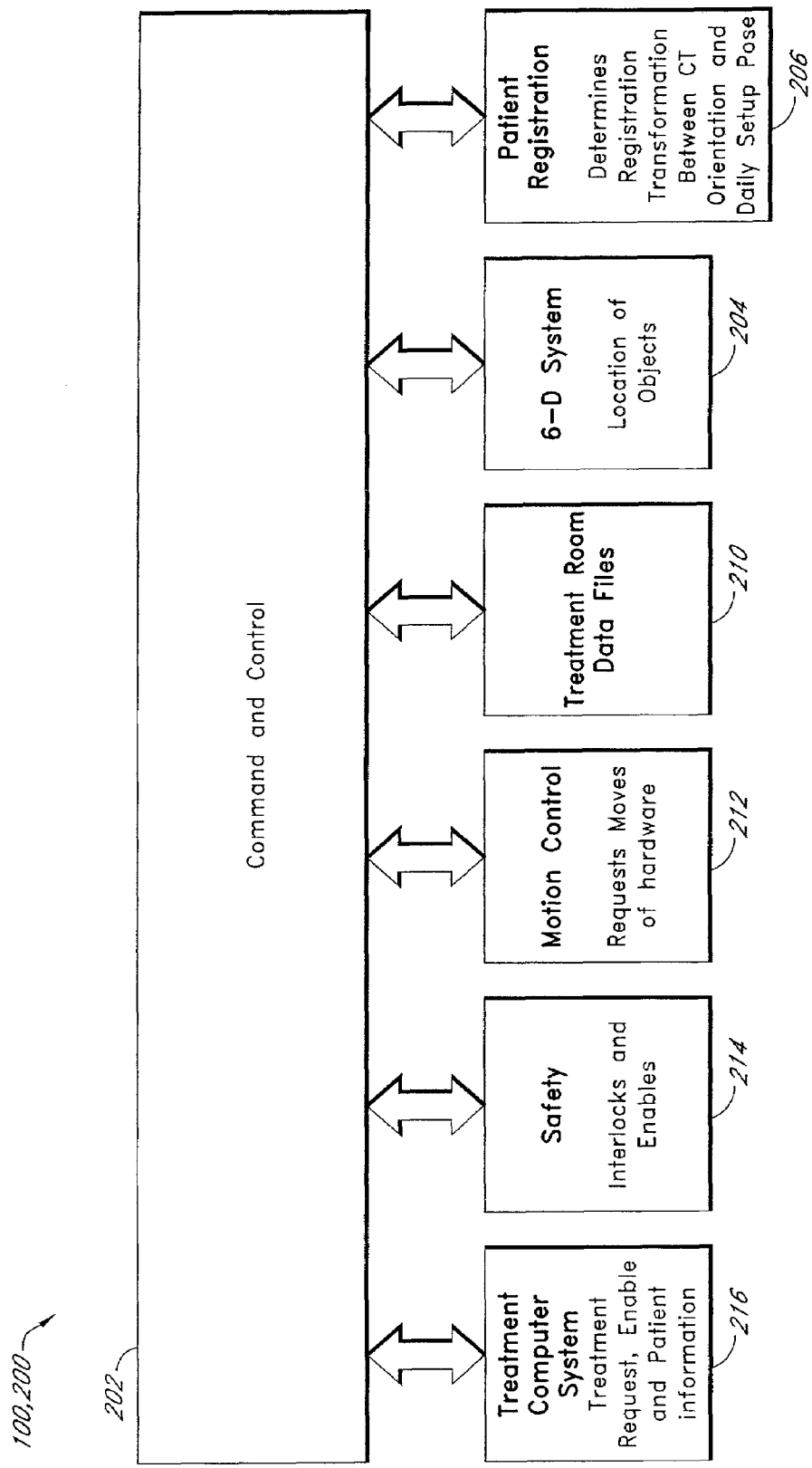
FIG. 8 is a block diagram of one embodiment of a precision patient positioning system of a radiation therapy system.

The system 100 also comprises, in this embodiment, a precision patient alignment system 200 which employs the location information provided in state 160 for the object(s). As illustrated in FIG. 8, the patient alignment system 200 comprises a command and control module 202 communicating with a 6D system 204, a patient registration module 206, data files 210, a motion control module 212, a safety module 214, and a user interface 216. The patient alignment system 200 employs location information provided by the 6D system 204 to more accurately register the patient and move the nozzle 104 and the patient positioner 114 to achieve a desired treatment pose as indicated by the prescription for the patient provided by the data files 210.

Figure 9:
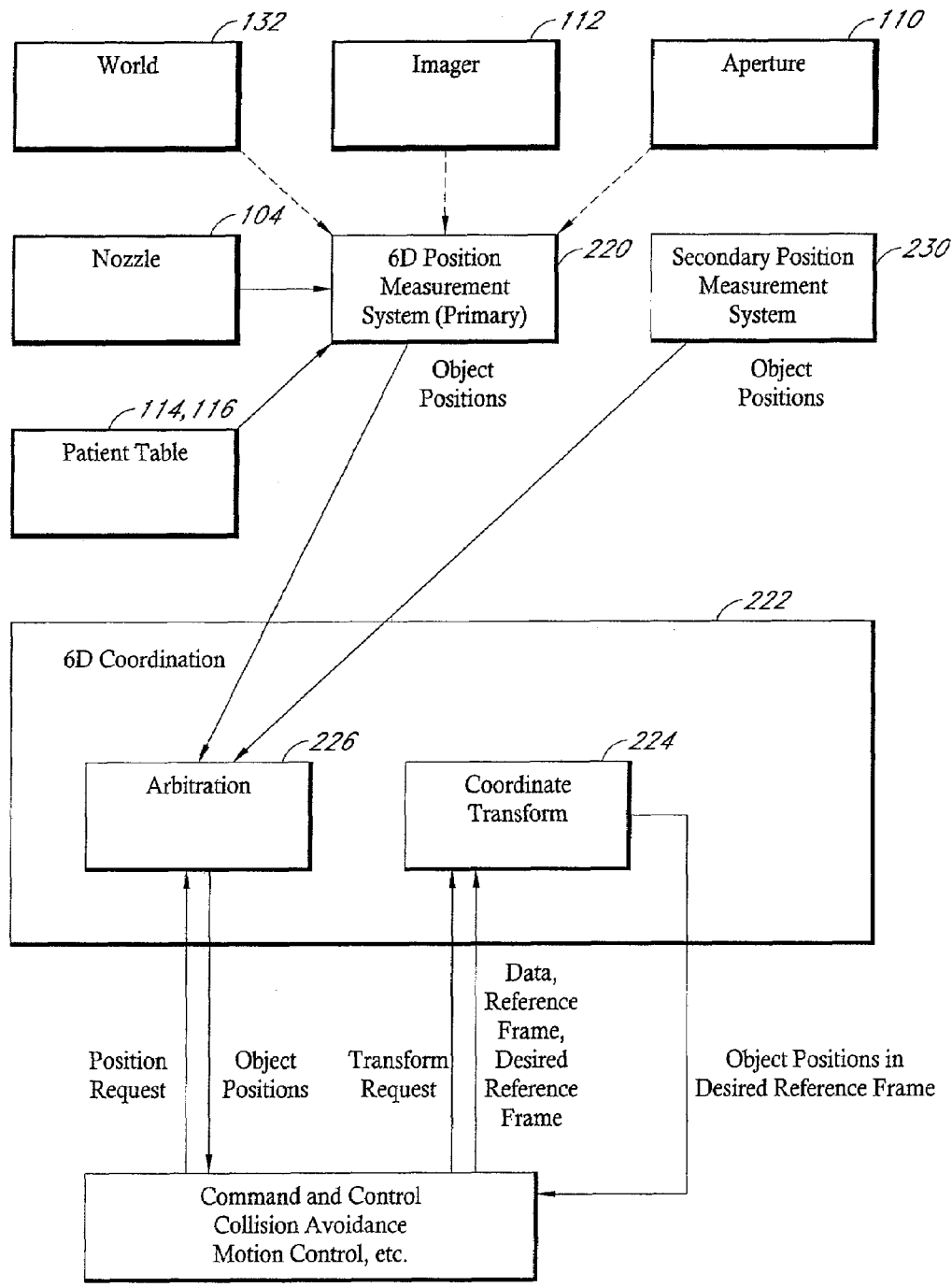
FIG. 9 is a block diagram of one embodiment of an external measurement and 6D coordination system of the patient positioning system.

In this embodiment, the 6D system 204 receives position data from the external measurement devices 124 and from the resolvers 134 relating to the current location of the nozzle 104, the aperture 110, the imager 112, the patient positioner 114, and patient pod 116, as well as the location of one or more fixed landmarks 132 indicated in FIG. 9 as the world 132. The fixed landmarks, or world, 132 provide a non-moving origin or frame of reference to facilitate determination of the position of the moving components of the radiation therapy system 100. This location information is provided to a primary 6D position measurement system 220 which then uses the observed data from the external measurement devices 124 and resolvers 134 to calculate position and orientation coordinates of these five components and origin in a first reference frame. This position information is provided to a 6D coordination module 222 which comprises a coordinate transform module 224 and an arbitration module 226. The coordinate transform module 224 communicates with other modules of the patient alignment system 200, such as the command and control module 202 and the motion control with path planning and collision avoidance module 212.

Depending on the stage of the patient registration and therapy delivery process, other modules of the patient alignment system 200 can submit calls to the 6D system 204 for a position request of the current configuration of the radiation therapy system 100. Other modules of the patient alignment system 200 can also provide calls to the 6D system 204 such as a coordinate transform request. Such a request typically will include submission of location data in a given reference frame, an indication of the reference frame in which the data is submitted and a desired frame of reference which the calling module wishes to have the position data transformed into. This coordinate transform request is submitted to the coordinate transform module 224 which performs the appropriate calculations upon the submitted data in the given reference frame and transforms the data into the desired frame of reference and returns this to the calling module of the patient alignment system 200.

For example, the radiation therapy system 100 may determine that movement of the patient positioner 114 is indicated to correctly register the patient. For example, a translation of plus 2 mm along an x-axis, minus 1.5 mm along a y-axis, no change along a z-axis, and a positive 1° rotation about a vertical axis is indicated. This data would be submitted to the coordinate transform module 224 which would then operate upon the data to return corresponding movement commands to the patient positioner 114. The exact coordinate transformations will vary in specific implementations of the system 100 depending, for example, on the exact configuration and dimensions of the patient positioner 114 and the relative position of the patient positioner 114 with respect to other components of the system 100. However, such coordinate transforms can be readily determined by one of ordinary skill in the art for a particular application.

The arbitration module 226 assists in operation of the motion control module 212 by providing specific object position information upon receipt of a position request. A secondary position measurement system 230 provides an alternative or backup position measurement function for the various components of the radiation therapy system 100. In one embodiment, the secondary position measurement system 230 comprises a conventional positioning functionality employing predicted position information based on an initial position and commanded moves. In one embodiment, the primary position measurement system 220 receives information from the external measurement devices 124 and the secondary position measurement system 230 receives independent position information from the resolvers 134. It will generally be preferred that the 6D measurement system 220 operate as the primary positioning system for the previously described advantages of positioning accuracy and speed.

Figure 10:
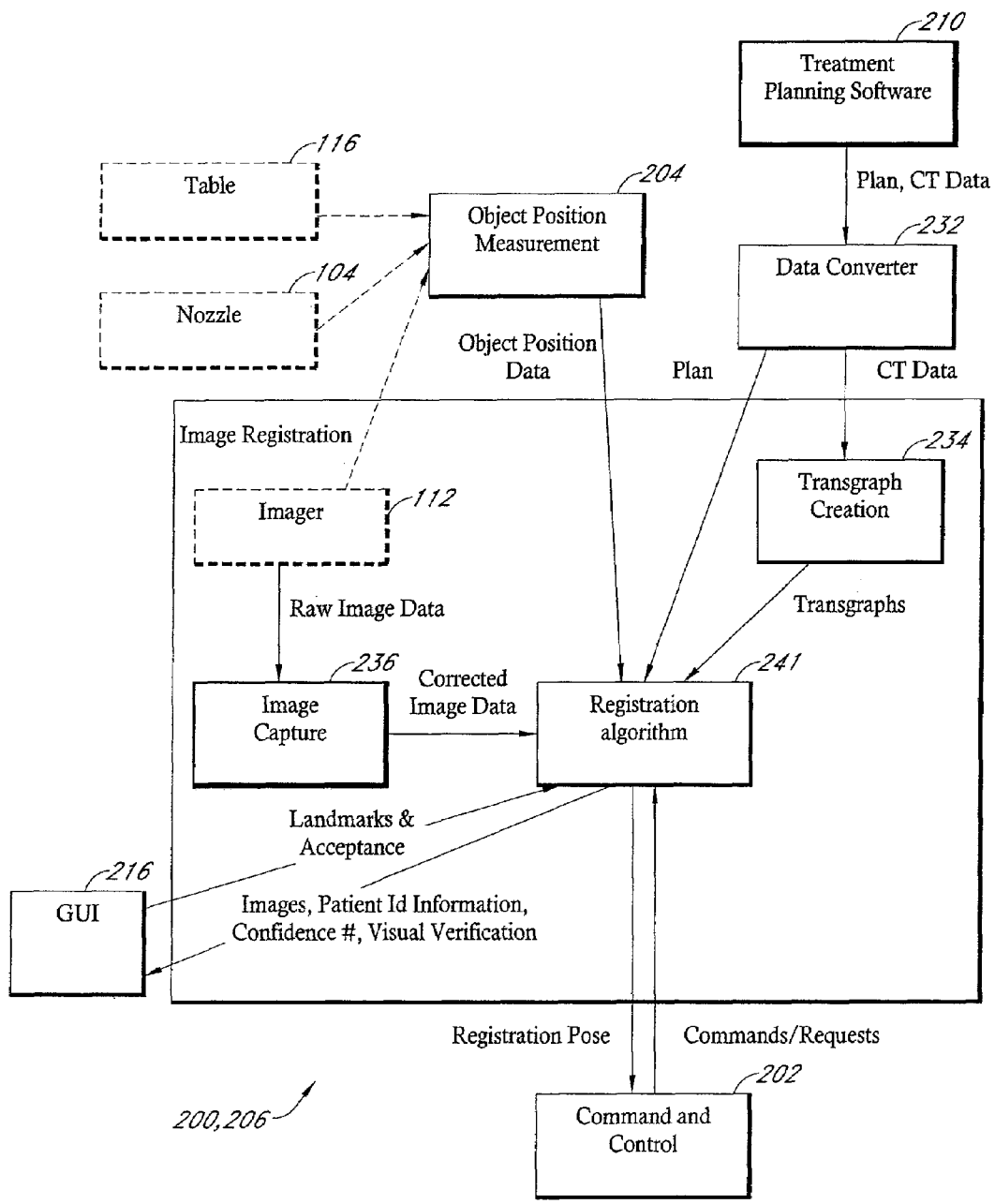
FIG. 10 is a block diagram of a patient registration module of the patient positioning system.

FIG. 10 illustrates in greater detail the patient registration module 206 of the patient alignment system 200. As previously described, the 6D system 204 obtains location measurements of various components of the radiation therapy system 100, including the table or patient pod 116 and the nozzle 104 and determines position coordinates of these various components and presents them in a desired frame of reference. The data files 210 provide information relating to the patient's treatment prescription, including the treatment plan and CT data previously obtained at a planning or prescription session. This patient's data can be configured by a data converter 232 to present the data in a preferred format. The imager 112 also provides location information to the 6D system 204 as well as to an image capture module 236. The image capture module 236 receives raw image data from the imager 112 and processes this data, such as with filtering, exposure correction, scaling, and cropping to provide corrected image data to a registration algorithm 241.

In this embodiment, the CT data undergoes an intermediate processing step via a transgraph creation module 234 to transform the CT data into transgraphs which are provided to the registration algorithm 241. The transgraphs are an intermediate data representation and increase the speed of generation of DRRs. The registration algorithm 241 uses the transgraphs, the treatment plan, the current object position data provided by the 6D system 204 and the corrected image data from the imager(s) 112 to determine a registered pose which information is provided to the command and control module 202. The registration algorithm 241 attempts to match either as closely as possible or to within a designated tolerance the corrected image data from the imager 112 with an appropriate DRR to establish a desired pose or to register the patient. The command and control module 202 can evaluate the current registered pose and provide commands or requests to induce movement of one or more of the components of the radiation therapy system 100 to achieve this desired pose. Additional details for a suitable registration algorithm may be found in the published doctoral dissertation of David A. LaRose of May 2001 submitted to Carnegie Mellon University entitled "Iterative X-ray/CT Registration Using Accelerated Volume Rendering" which is incorporated herein in its entirety by reference.

Figure 11:
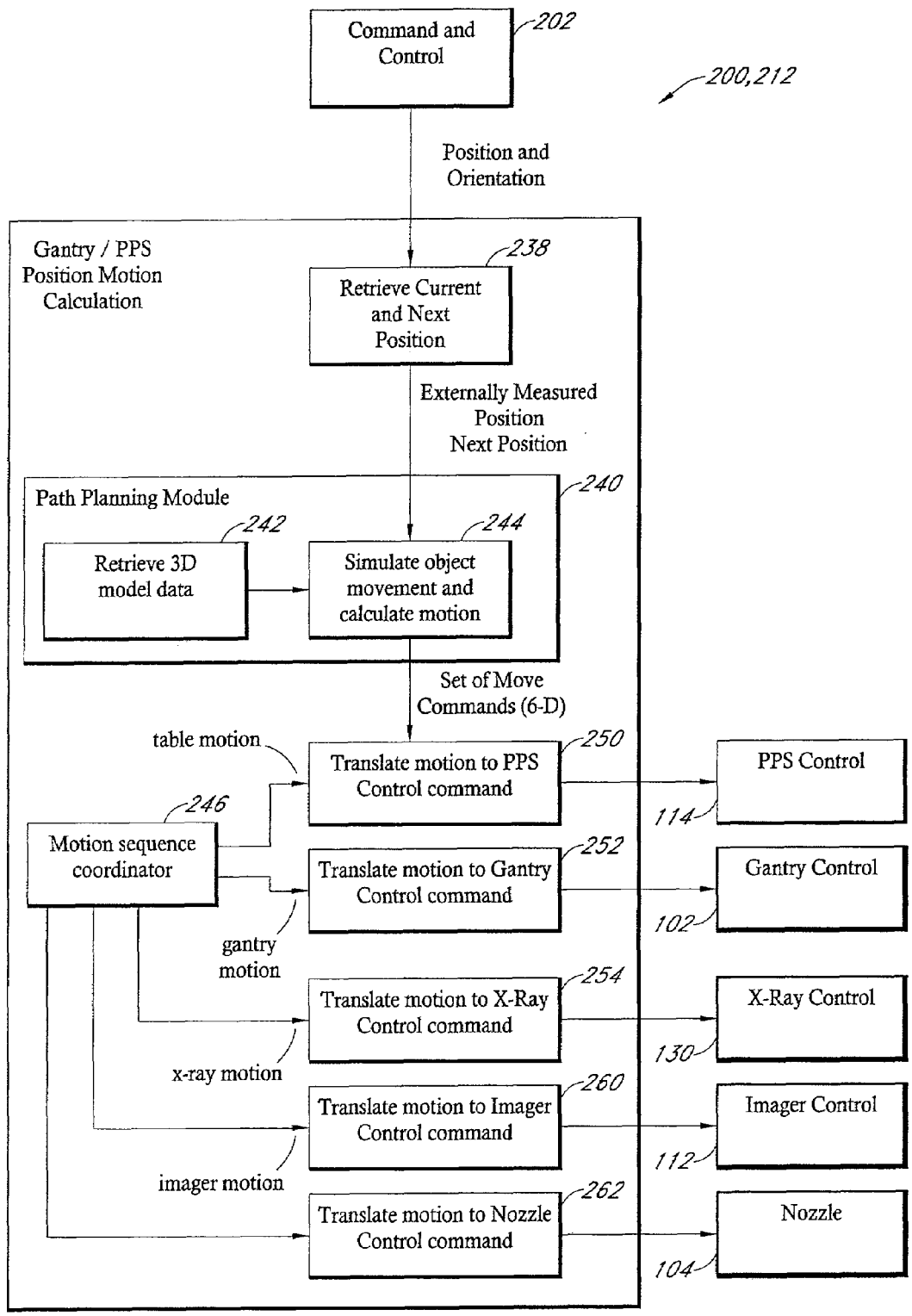
FIG. 11 is a block diagram of a path planning module of a motion control module of the patient positioning system.
Figure 12:
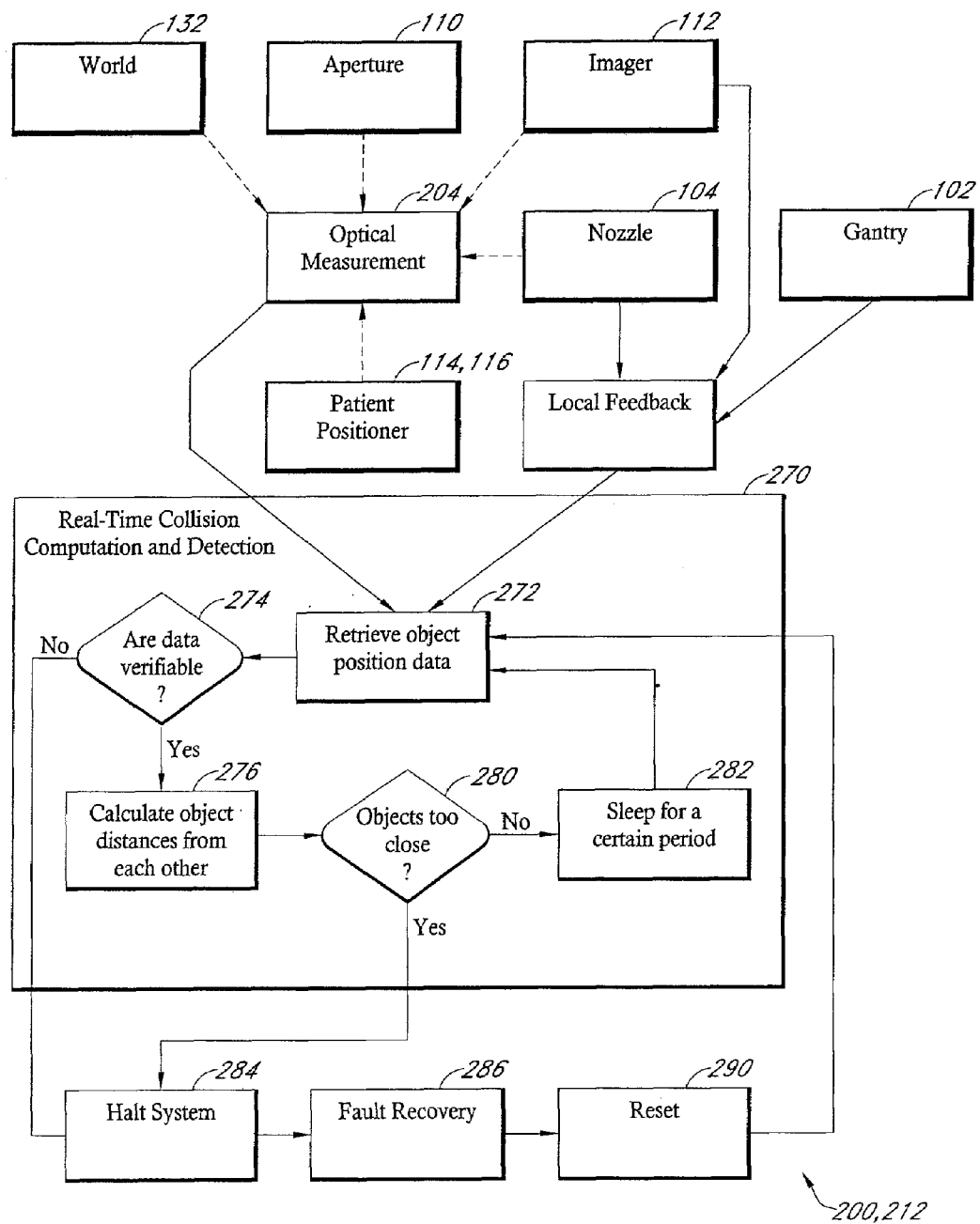
FIG. 12 is a block diagram of an active collision avoidance module of the motion control module of the patient positioning system.
Figure 13:
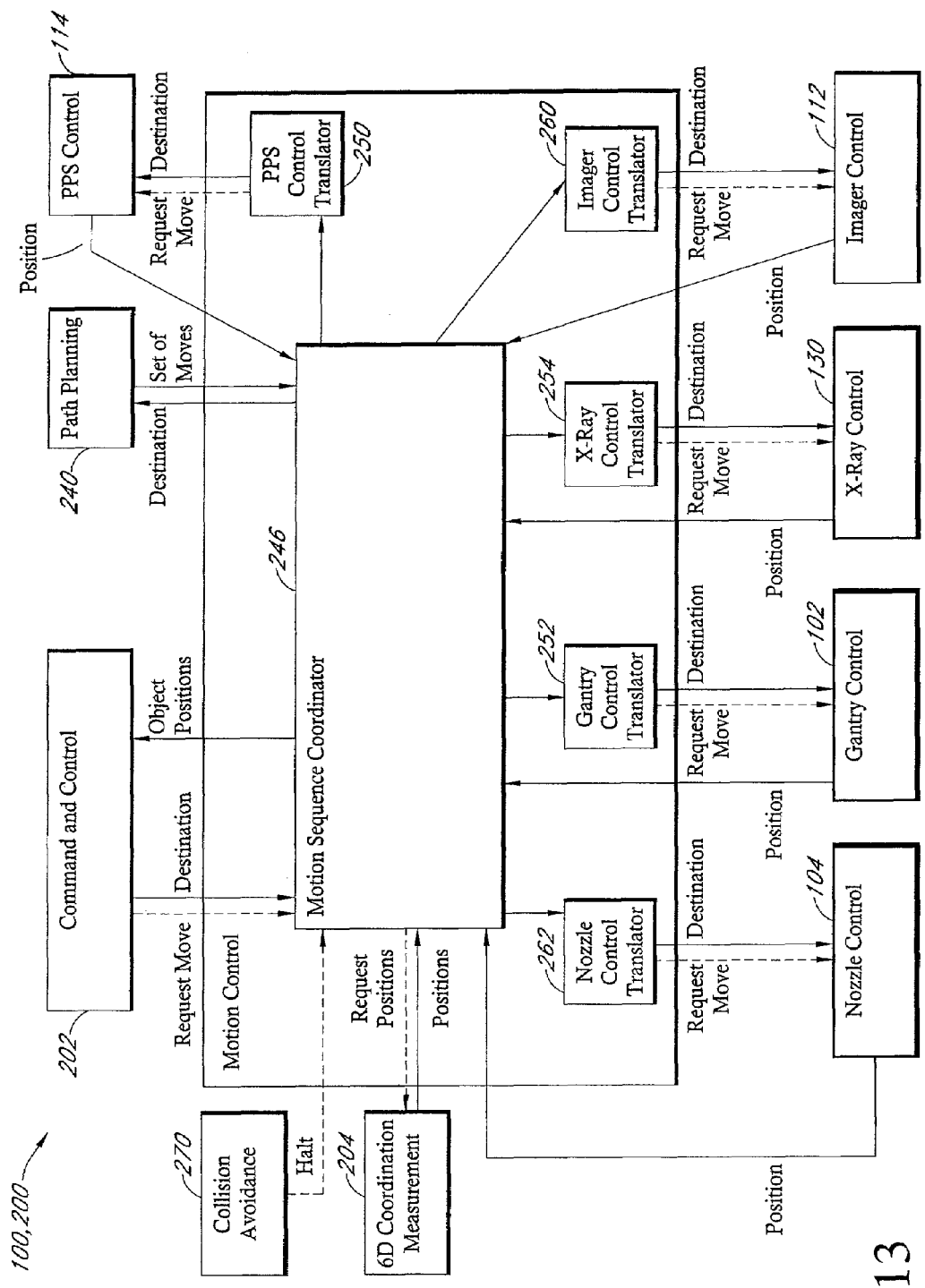
FIG. 13 is a block diagram of one embodiment of the collision avoidance module and a motion sequence coordinator of a motion control module.

FIGS. 11-13 illustrate embodiments with which the system 100 performs this movement. FIG. 11 illustrates that the command and control module 202 has provided a call for movement of one or more of the components of the radiation therapy system 100. In state 238, the motion control module 212 retrieves a current position configuration from the 6D system 204 and provides this with the newly requested position configuration to a path planning module 240. The path planning module 240 comprises a library of three-dimensional model data which represent position envelopes defined by possible movement of the various components of the radiation therapy system 100. For example, as previously described, the imager 112 is retractable and a 3D model data module 242 indicates the envelope or volume in space through which the imager 112 can move depending on its present and end locations.

The path planning module 240 also comprises an object movement simulator 244 which receives data from the 3D model data module 242 and can calculate movement simulations for the various components of the radiation therapy system 100 based upon this data. This object movement simulation module 244 preferably works in concert with a collision avoidance module 270 as illustrated in FIG. 12. FIG. 12 again illustrates one embodiment of the operation of the 6D system 204 which in this embodiment obtains location measurements of the aperture 110, imager 112, nozzle 104, patient positioner and patient pod 114 and 116 as well as the fixed landmarks or world 132. FIG. 12 also illustrates that, in this embodiment, local feedback is gathered from resolvers 134 corresponding to the patient positioner 114, the nozzle 104, the imager 112, and the angle of the gantry 102.

This position information is provided to the collision avoidance module 270 which gathers the object information in an object position data library 272. This object data is provided to a decision module 274 which evaluates whether the data is verifiable. In certain embodiments, the evaluation of the module 274 can investigate possible inconsistencies or conflicts with the object position data from the library 272 such as out-of-range data or data which indicates, for example, that multiple objects are occupying the same location. If a conflict or out-of-range condition is determined, e.g., the result of the termination module 274 is negative, a system halt is indicated in state 284 to inhibit further movement of components of the radiation therapy system 100 and further proceeds to a fault recovery state 286 where appropriate measures are taken to recover or correct the fault or faults. Upon completion of the fault recovery state 286, a reset state 290 is performed followed by a return to the data retrieval of the object position data library in module 272.

If the evaluation of state 274 is affirmative, a state 276 follows where the collision avoidance module 270 calculates relative distances along current and projected trajectories and provides this calculated information to an evaluation state 280 which determines whether one or more of the objects or components of the radiation therapy system 100 are too close. If the evaluation of stage 280 is negative, e.g., that the current locations and projected trajectories do not present a collision hazard, a sleep or pause state 282 follows during which movement of the one or more components of the radiation therapy system 100 is allowed to continue as indicated and proceeds to a recursive sequence through modules 272, 274, 276, 280, and 282 as indicated.

However, if the results of the evaluation state 280 are affirmative, e.g., that either one or more of the objects are too close or that their projected trajectories would bring them into collision, the system halt of state 284 is implemented with the fault recovery and reset states 286 and 290, following as previously described. Thus, the collision avoidance module 270 allows the radiation therapy system 100 to proactively evaluate both current and projected locations and movement trajectories of movable components of the system 100 to mitigate possible collisions before they occur or are even initiated. This is advantageous over systems employing motion stops triggered, for example, by contact switches which halt motion upon activation of stop or contact switches, which by themselves may be inadequate to prevent damage to the moving components which can be relatively large and massive having significant inertia, or to prevent injury to a user or patient of the system.

Assuming that the object movement simulation module 244 as cooperating with the collision avoidance module 270 indicates that the indicated movements will not pose a collision risk, the actual movement commands are forwarded to a motion sequence coordinator module 246 which evaluates the indicated movement vectors of the one or more components of the radiation therapy system 100 and sequences these movements via, in this embodiment, five translation modules. In particular, the translation modules 250, 252, 254, 260, and 262 translate indicated movement vectors from a provided reference frame to a command reference frame appropriate to the patient positioner 114, the gantry 102, the x-ray source 130, the imager 112, and the nozzle 104, respectively.

As previously mentioned, the various moveable components of the radiation therapy system 100 can assume different dimensions and be subject to different control parameters and the translation modules 250, 252, 254, 260, and 262 interrelate or translate a motion vector in a first frame of reference into the appropriate reference frame for the corresponding component of the radiation therapy system 100. For example, in this embodiment the gantry 102 is capable of clockwise and counterclockwise rotation about an axis whereas the patient positioner 114 is positionable in six degrees of translational and rotational movement freedom and thus operates under a different frame of reference for movement commands as compared to the gantry 102. By having the availability of externally measured location information for the various components of the radiation therapy system 100, the motion sequence coordinator module 246 can efficiently plan the movement of these components in a straightforward, efficient and safe manner.

Figure 14:
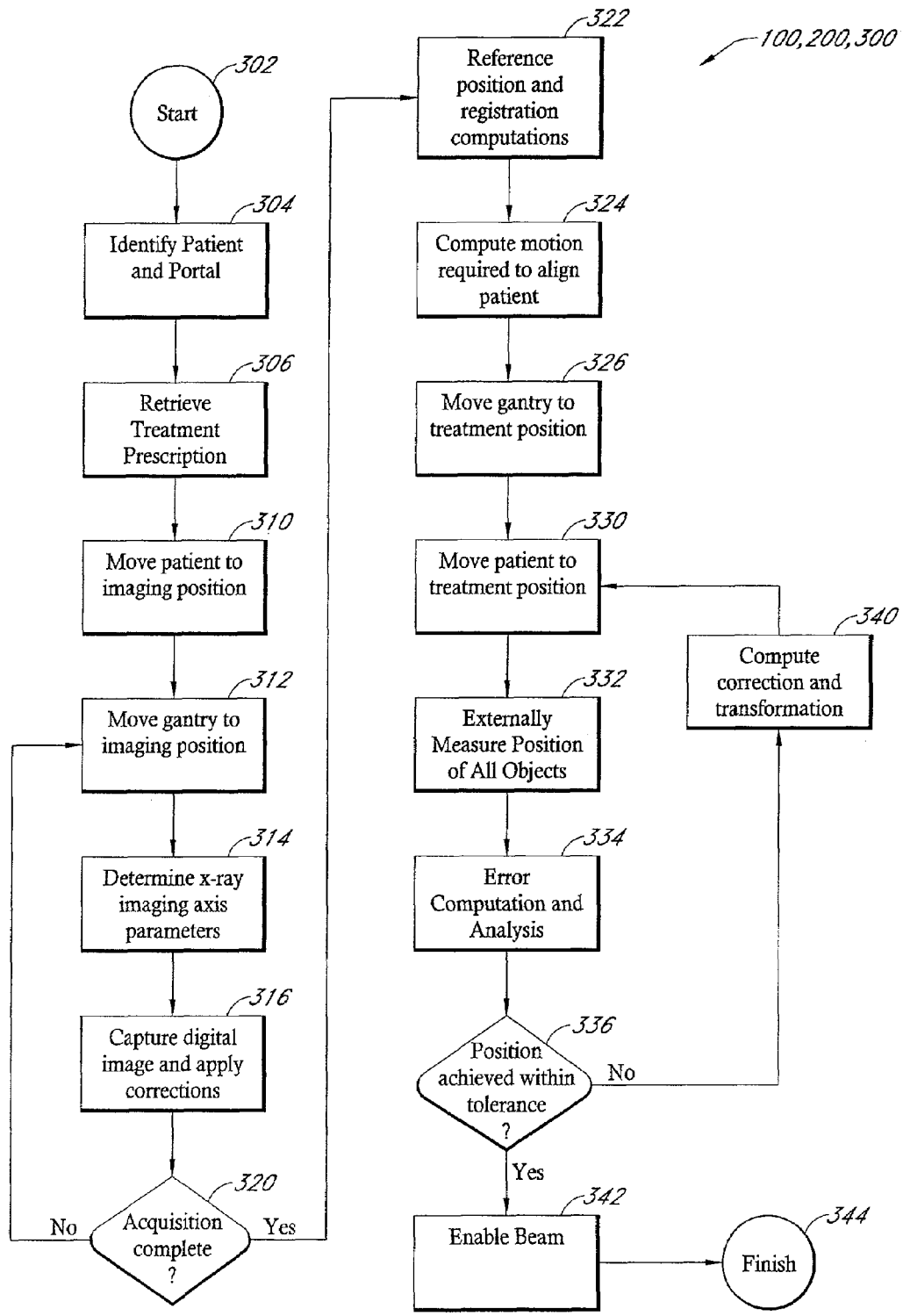
FIG. 14 is a flow chart of the operation of one embodiment of a method of positioning a patient and delivering radiation therapy.

FIG. 14 illustrates a workflow or method 300 of one embodiment of operation of the radiation therapy system 100 as provided with the patient alignment system 200. From a start state 302, follows an identification state 304 wherein the particular patient and treatment portal to be provided is identified. This is followed by a treatment prescription retrieval state 306 and the identification and treatment prescription retrieval of states 304 and 306 can be performed via the user interface 216 and accessing the data files of module 210. The patient is then moved to an imaging position in state 310 by entering into the patient pod 116 and actuation of the patient positioner 114 to position the patient pod 116 securing the patient in the approximate position for imaging. The gantry 102, imager(s) 112, and radiation source(s) 130 are also moved to an imaging position in state 312 and in state 314 the x-ray imaging axis parameters are determined as previously described via the 6D system 204 employing the external measurement devices 124, cooperating markers 122, and resolvers 134.

In state 316, a radiographic image of the patient is captured by the imager 112 and corrections can be applied as needed as previously described by the module 236. In this embodiment, two imagers 112 and corresponding x-ray sources 130 are arranged substantially perpendicularly to each other. Thus, two independent radiographic images are obtained from orthogonal perspectives. This aspect provides more complete radiographic image information than from a single perspective. It will also be appreciated that in certain embodiments, multiple imaging of states 316 can be performed for additional data. An evaluation is performed in state 320 to determine whether the radiographic image acquisition process is complete and the determination of this decision results either in the negative case with continuation of the movement of state 312, the determination of state 314 and the capture of state 316 as indicated or, when affirmative, followed by state 322.

In state 322, external measurements are performed by the 6D system 204 as previously described to determine the relative positions and orientations of the various components of the radiation therapy system 100 via the patient registration module 206 as previously described. In state 324, motion computations are made as indicated to properly align the patient in the desired pose.

While not necessarily required in each instance of treatment delivery, this embodiment illustrates that in state 326 some degree of gantry 102 movement is indicated to position the gantry 102 in a treatment position as well as movement of the patient, such as via the patient positioner 114 in state 330 to position the patient in the indicated pose. Following these movements, state 332 again employs the 6D system 204 to externally measure and in state 334 to compute and analyze the measured position to determine in state 336 whether the desired patient pose has been achieved within the desired tolerance. If adequately accurate registration and positioning of the patient has not yet been achieved, state 340 follows where a correction vector is computed and transformed into the appropriate frame of reference for further movement of the gantry 102 and/or patient positioner 114. If the decision of state 336 is affirmative, e.g., that the patient has been satisfactorily positioned in the desired pose, the radiation therapy fraction is enabled in state 342 in accordance with the patient's prescription. For certain patient prescriptions, it will be understood that the treatment session may indicate multiple treatment fractions, such as treatment from a plurality of orientations and that appropriate portions of the method 300 may be iteratively repeated for multiple prescribed treatment fractions. However, for simplicity of illustration, a single iteration is illustrated in FIG. 14. Thus, following the treatment delivery of state 342, a finished state 344 follows which may comprise the completion of treatment for that patient for the day or for a given series of treatments.

Thus, the radiation therapy system 100 with the patient alignment system 200, by directly measuring movable components of the system 100, employs a measured feedback to more accurately determine and control the positioning of these various components. A particular advantage of the system 100 is that the patient can be more accurately registered at a treatment delivery session than is possible with known systems and without an iterative sequence of radiographic imaging, repositioning of the patient, and subsequent radiographic imaging and data analysis. This offers the significant advantage both of more accurately delivering the therapeutic radiation, significantly decreasing the latency of the registration, imaging and positioning processes and thus increasing the possible patient throughput as well as reducing the exposure of the patient to x-ray radiation during radiographic imaging by reducing the need for multiple x-ray exposures during a treatment session.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A therapy delivery system, the system comprising:
   a patient positioning structure configured to position a patient in multiple translational and multiple rotational axes and secure at least a portion of the patient substantially immobile at a desired treatment pose;
   a therapy delivery assembly configured to deliver therapy along a delivery path, wherein at least one of the patient positioning structure and the therapy delivery assembly are movable to align the desired treatment pose of a therapy delivery target of the patient with the therapy delivery path and wherein a movement envelope of at least one of the patient positioning structure and the therapy delivery assembly intersects one or more other structures of the therapy delivery system;
   a plurality of external measurement devices which obtain location measurements of at least the patient positioning structure and the therapy delivery assembly;
   a motion sequence coordinator adapted to control the movement of at least one of the positioning structure and the therapy delivery assembly in response to a first movement command for at least one of the patient positioning structure and the therapy delivery assembly to position the patient in the desired pose; and
   a controller which receives the location measurements of at least the patient positioning structure and the therapy delivery assembly from the plurality of external measurement devices and determines the first movement command and determines whether a collision is indicated for the first movement command and, if no collision is indicated, initiates a corresponding first movement by forwarding the first movement command to the motion sequence coordinator.

2. The system of claim 1, wherein the external measurement devices obtain optical images to obtain the location measurements.

3. The system of claim 1, further comprising a plurality of markers fixed to at least the patient positioning structure and the therapy delivery assembly and wherein the external measurement devices obtain location measurements of the markers.

4. The system of claim 1, further comprising at least one local position feedback device in operative communication with at least one of the patient positioning structure and the therapy delivery assembly wherein the at least one local position feedback device provides supplemental location data to the controller indicative of the location of the at least one of the patient positioning structure and the therapy delivery assembly.

5. The system of claim 1, further comprising a movable patient imaging system configured to obtain an image of the patient and wherein the controller determines the relative pose of the therapy delivery target with respect to the therapy path at least in part with image data from the patient imaging system.

6. The system of claim 1, wherein both the patient positioning structure and the therapy delivery assembly are movable and wherein the system determines the movement commands for concurrent movement of the patient positioning structure and the therapy delivery assembly to increase speed of acquisition of the desired pose.

7. The system of claim 1, wherein the external measurement devices also determines location of fixed objects adjacent the system and wherein the controller inhibits motion if any collision with such objects is indicated.

8. A path planning and collision avoidance control system for a therapy system, the control system comprising:
   a plurality of external measurement devices arranged to obtain location measurements of components of the therapy system; and
   a controller receiving location information from the plurality of external measurement devices and providing movement commands to movable components of the therapy system to automatically align the patient in multiple translational and multiple rotational axes in a desired translational and rotational pose wherein a movement envelope of at least some of the movable components intersect other components of the therapy system and wherein, upon receiving a first movement command and prior to initiating a corresponding first movement, the controller further determines a corresponding movement envelope of the movable components and wherein the controller evaluates the movement envelope to determine if a collision is indicated and initiates the first movement of the movable components if no collision is indicated.

9. The control system of claim 8, wherein aligning the patient in the desired pose comprises aligning a patient support with respect to a therapy aiming point to which the therapy system directs therapy.

10. The control system of claim 8, further comprising a movable patient imager system configured to obtain an image of the patient and a target isocenter, wherein the controller determines movement commands and trajectories for both the patient imager and other movable components subject to the movement commands and inhibits movement if a collision is indicated.

11. The control system of claim 8, further comprising a plurality of markers fixed to selected points of the therapy system and wherein the external measurement devices obtain location measurements of the markers.

12. The control system of claim 11, wherein multiple external measurement devices obtain position measurements of a single marker so as to provide location data from multiple perspectives.

13. The control system of claim 8, wherein the external measurement devices also monitor for objects that may enter the determined movement envelope and wherein the controller inhibits motion if any collision with such objects is indicated.

14. A method of registering and positioning a patient for delivery of therapy, the method comprising the steps of:
   positioning a patient in an initial pose with a patient positioner, wherein the patient positioner is capable of movement in multiple translational and multiple rotational axes;
   externally measuring the locations of selected points of the patient positioner and a movable therapy delivery assembly, wherein a movement envelope of the patient positioner and of the therapy delivery assembly intersect at least one of each other and other components proximate the patient positioner and the therapy delivery assembly;
   determining a difference vector between the observed initial pose and a desired treatment pose with respect to the therapy delivery assembly;
   determining a corresponding first movement command and a movement trajectory to bring the patient to the desired treatment pose with respect to the therapy delivery assembly; and
   comparing the movement trajectory with the measured locations of the selected points prior to initiating a corresponding first movement and initiating the first movement by performing the indicated first movement command if no collision is indicated.

15. The method of claim 14, wherein externally measuring the location of the selected points comprises employing a plurality of cameras to obtain optical images of the selected points.

16. The method of claim 14, wherein the difference vector is determined in a first reference frame and wherein determining the movement commands comprises transforming the difference vector in the first reference frame into a corresponding movement vector in a second reference frame.

17. The method of claim 14, further comprising, prior to initiating movement, evaluating the externally measured locations and inhibiting movement and triggering a fault recovery state when an inconsistency or conflict is indicated in the externally measured locations.

18. The method of claim 14, further comprising obtaining radiographic image data of the patient and wherein the determining the movement vector and the corresponding movement commands is based at least in part on the obtaining radiographic data.

19. The method of claim 14, further comprising:
   determining multiple direction vectors of the selected points;
   determining intersections of the multiple direction vectors; and
   determining rotational orientations such that the locations comprise both a translational and rotational dimension.

20. The method of claim 14, comprising externally measuring the locations of at least some of the selected points from multiple perspectives.

21. The method of claim 14, further comprising monitoring the movement trajectory for possible intrusion of foreign objects and inhibiting movement if such intrusion of foreign object occurs.

* * * * *